United States Patent [19]

Thompson et al.

[11] Patent Number: 5,756,508
[45] Date of Patent: *May 26, 1998

[54] MUSCARINE ANTAGONISTS

[75] Inventors: Wayne J. Thompson, Lansdale; Richard W. Ransom, New Britain; Pierre Mallorga, Lansdale; Michael F. Sugrue, Blue Bell, all of Pa.

[73] Assignee: Merck & Co., Inc., Rahway, N.J.

[*] Notice: The term of this patent shall not extend beyond the expiration date of Pat. No. 5,574,044.

[21] Appl. No.: 736,704

[22] Filed: Oct. 28, 1996

[51] Int. Cl.$^6$ .............. C07D 211/14; C07D 235/26; C07D 239/26; A61K 31/415

[52] U.S. Cl. .......... 514/256; 514/304; 514/316; 514/317; 514/318; 514/323; 544/333; 546/125; 546/126; 546/186; 546/187

[58] Field of Search .................. 514/256, 304, 514/316; 544/333; 546/125, 126, 186, 187

[56] References Cited

U.S. PATENT DOCUMENTS 4,066,772  1/1978  Vandenberk et al. ............... 424/267
5,122,522  6/1992  Laties et al. ............... 514/220
5,284,843  2/1994  Stone et al. ............... 514/213
5,574,044  11/1996  Thompson et al. ............... 514/316

FOREIGN PATENT DOCUMENTS

WO 90/15604  of 0000  WIPO .

OTHER PUBLICATIONS

R. Feifel, et al., *Br. J. Pharmacol.* 99, pp. 455–460 (1990).
F. Dorje, et al., *J. Pharmacol. and Exp. Thera.*, 256(2), pp. 727–733 (1991).
O. Cervinka and P. Malon, *Chem. Commun.*, 42, pp (1977).
D. L. Commins and J. D. Brown, *Tetra Ltrs.*, 27(38), pp. 4549–4552 (1986).

*Primary Examiner*—Mukund J. Shah
*Assistant Examiner*—Deepak R. Rao
*Attorney, Agent, or Firm*—Sylvia A. Ayler; Mark R. Daniel

[57] ABSTRACT

This invention is concerned with novel 1,3-dihydro-1-[1-(1-heteroarylpiperidin-4-yl)piperidin-4-yl]-2H-benzimidazolones, derivatives thereof, their preparation, method of use and pharmaceutical compositions. These compounds are endowed with antimuscarinic activity and are useful in the treatment and/or prevention of myopia (commonly known as nearsightedness).

12 Claims, No Drawings

MUSCARINE ANTAGONISTS

This application claims the benefit of U.S. Provisional Application Ser. No. 60/007,098, filed Oct. 31, 1995.

BACKGROUND OF THE INVENTION

This invention relates to control of ocular development in general and, more particularly, to the treatment of the eye to prevent and/or arrest the development of myopia (nearsightedness). Approximately one of every four persons suffer from myopia, i.e., an elongation of the eye along the visual axis. In particular, myopia afflicts 10% to 75% of the youth of the world, depending upon race, geographic distribution and level of education. Myopia is not a trivial maldevelopment of the eye. In its pathologic form, the sclera continues to grow and as result the retina stretches and degenerates resulting in permanent blindness.

Inheritance, environmental forces such as diet, sun intake, and substantial eye use, etc., are but a few theories that have been postulated to explain the on-set of myopia. In that regard, preventive measures such as eye rest, eye exercise, eye glasses, contact lens and drug and surgical therapies have been proposed. However, these measures are neither ideal nor risk-free. The surgical therapies (e.g. corneal surgery using excimer lasers or conventional knives) attempted for this condition are drastic and often unsuccessful. Moreover, neither of the therapies (excimer lasers or conventional knives) are easily reversed or sufficiently predictable in their results. Complications from contact lens wear range from allergic reactions to permanent loss of vision due to corneal ulceration. Even with the complications associated with contact lens wear, there are roughly 24 million wearers in the U.S., with the number expected to double in the next 3 years. While eyeglasses eliminate most of the medical risks listed above, they are not an acceptable option as evidenced by the contact lens wearers who tolerate the frustration of contact lens wear.

One particular drug therapy utilized in the treatment of myopia involves the use of cycloplegics. Cycloplegics are topically administered drugs that relax the ciliary muscle of the eye, which is the muscle that focuses the eye by controlling lens dimensions. The classic cycloplegic drug is the belladonna alkaloid atropine, available for over a century. Atropine is a long-acting non-specific antimuscarinic agent that antagonizes the action of the neurotransmitter acetylcholine (ACh) at autonomic effector cells innervated by postganglionic cholinergic nerves of the parasympathetic nervous system. However, use of atropine, is impractical in that it causes mydriasis (increase of pupil size) and its action on the ciliary muscle to inhibit ocular focusing impairs near visual work like reading. There is strong evidence that the receptors in the iris and ciliary muscle responsible for the side effects of atropine are of the m3 subtype. Additionally, studies have shown that muscarinic receptors in the retina of a variety of non-human species are comprised of m1, m2 and m4 subtypes. Accordingly, a muscarinic antagonist with low m3 activity would be efficacious in prevention of the development of myopia without the undesirable side effects associated with the use of atropine.

There is now substantial evidence to link the posterior part of the eye, specifically image quality at the retina and hence an extension of the nervous system, to the postnatal regulation of ocular growth. There is significant evidence of myopia in an eye that is subjected to retinal image impairment. It has been shown that axial myopia can be experimentally induced, in either birds or primates, in an eye in which the retina is deprived of formed images, e.g., by suturing the eyelids or wearing an image diffusing goggle. The experimental myopia induced in birds or primates such as monkeys mimics, in many respects, the axial myopia of humans.

Thus, the phenomenon of an animal's vision process apparently contributes to the feedback mechanism by which postnatal ocular growth is normally regulated and refractive error is determined. This indicates that this mechanism is neural and likely originates in the retina. R. A. Stone, et al. have found a method of controlling the abnormal postnatal growth of the eye of a maturing animal. The method comprises controlling the presence of a neurochemical, its agonist or antagonist, which neurochemical is found to be changed under conditions during maturation leading to abnormal axial length. See U.S. Pat. No. 4,066,772 and 5,284,843. Therein it is disclosed that retinal concentrations of dopamine were found to be reduced during such image deprivation and the ocular administration of a dopamine-related agent, e.g., apomorphine, a dopamine agonist, was found to inhibit or actually prevent the axial enlargement of the eye under conditions ordinarily leading to such enlargement.

There have also been recent advances made in the understanding of the cholinergic nervous system and the receptors thereto. Cholinergic receptors are proteins embedded in the wall of a cell that respond to the chemical acetylcholine. Particularly, it is now known that the cholinergic receptors are subdivided into nicotinic and muscarinic receptors and that the muscarinic receptors are not all of the same type. Recent literature indicates that there are at least five types of cholinergic muscarinic receptors (types m1 through m5). Receptors of type m1 are those present in abundance and thought to be enriched in the brain neural tissue and neural ganglia. The other receptors are concentrated in other tissues such as the heart, smooth muscle tissue or glands. While many pharmacological agents interacting with muscarinic receptors influence several types of receptors, some agents are known to have a major effect on a single type of receptor with relative selectivity. Still other agents may have a significant effect on more than one or even all types of receptors.

It is known, for example, that pirenzepine, (Gastrozepin, LS 519)5, 11-Dihydro-11-[4-methyl-1-piperazinyl)acetyl]-6H-pyrido[2,3-b]benzodiazepin-6-one, and its dihydrochloride are anticholinergic, antimuscarinic, and relatively selective for m1 receptors. See U.S. Pat. No. 5,122,522 and WO9015604-A. It is also known that 4-DAMP (4-diphenylacetoxy-N-methylpiperadine methiodide) is a relatively selective antagonist for smooth muscle (ordinarily called m3 type but variously called type m2 or m3, as the current classification of receptors is in flux). Pirenzepine, being primarily an m1 antagonist, inhibits axial elongation, but is far less effective at pupil dilation than atropine or another cycloplegic agent. This makes it possible to suppress the development of myopia without dilating the pupil and paralyzing the accommodation activity of the ciliary muscle. Additionally, the administration of a drug topically into the eye of a developing child for a long period of time makes it desirable to have a minimal likelihood of sensitization of the eye. Pirenzepine and atropine test positive in sensitization assays and this is an undesirable side effect.

It is therefore an object of this invention to provide a muscarinic antagonist which is effective in the treatment and prevention of myopia without many side effects.

SUMMARY OF THE INVENTION

This invention is concerned with novel 1,3-dihydro-1-[1-(1-heteroarylpiperidin-4-yl)piperidin-4-yl]-2H- benzimidazolones, their compositions and method of use. The novel compounds are selective muscarinic antagonists of the m1, m2, and m4 subtypes with low activity at the m3 subtype. The compounds have good ocular penetration (bioavailability) when dosed as a 0.1-4% aqueous solution, preferably a 0.5-2% solution. The compounds are effective for the treatment and/or prevention of myopia.

DETAILED DESCRIPTION OF THE INVENTION

The novel compounds of this invention are represented by the structural formula I:

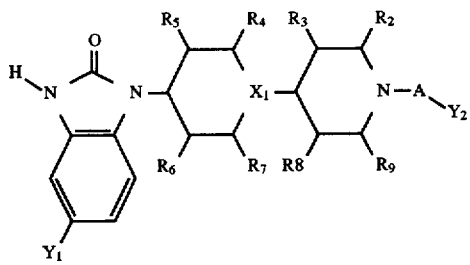

or pharmaceutically acceptable salts thereof, or diastereomers, enantiomers or mixtures thereof; wherein:

$R_2$–$R_9$ are independently H, alkyl, halo, alkoxy, OH, HOCH2—, aryl, 3-pyridyl, 5-pyrimidinyl, alkoxycarbonyl, amino, dialkylamino, alkene, thioalkyl, or alkylamino; alternatively, $R_4$ and $R_7$ or $R_2$ and $R_9$ may be connected as an ethylene bridge to form a bicyclic heterocycle;

$Y_1$ is H, alkyl, halo, alkylamino, dialkylamino, alkoxy, alkoxyamino, or amino;

$Y_2$ is heterocycle, or heterocyclyl;

A is H, CHR$_1$, C(R$_1$)$_2$ or carbonyl;

$R_1$ is alkyl, alkoxy, aryl, heteroaryl, heterocyclyl or heterocycle; and $X_1$ is N or C.

The term heterocycle or heterocyclic, as used herein except where noted, represents a stable 5- to 7- membered monocyclic heterocyclic ring, which is either saturated or unsaturated, and which consists of carbon atoms and from one to three heteroatoms selected from the group consisting of N, O and S, and including any bicyclic group in which any of the above defined heterocyclic rings is fused to a benzene ring. The heterocyclic ring may be attached at any heteroatom or carbon atom which results in the creation of a stable structure. Examples of such heterocyclic rings include pyridine, pyrazine, pyrimidine, pyridazine, triazine, imidazole, pyrazole, triazole, quinoline, isoquinoline, quinazoline, quinoxaline, phthalazine, oxazole, isoxazole, thiazole, isothiazole, thiadiazole, oxadiazole, pyrrole, furan, thiophene, hydrogenated derivatives of these heterocyles such as piperidine, pyrrolidine, azetidine, tetrahydrofuran, and N-oxide derivatives of heterocyles containing basic nitrogen. Any fused combinations of any of these above-defined heterocyclic rings is also a part of this definition. Attached to the heterocyclic ring can be substituents such as alkyls, amines, alkylamino, or halogens (F, Cl, Br, I).

The term alkyl is intended to include branched, cyclic and straight chain saturated aliphatic hydrocarbon groups having 1 to 15 carbon atoms, unless otherwise defined. Preferred straight or branched alkyl groups include methyl, ethyl, propyl, isopropyl, butyl, t-butyl and the like. Preferred cycloalkyl groups include cyclopentyl and cyclohexyl.

The term alkoxy represents an alkyl group of indicated carbon atoms attached through an oxygen linkage.

The term alkylamino represents an alkyl group of indicated carbon atoms attached through a nitrogen atom linkage.

The term dialkylamino represents two alkyl groups of indicated carbon atoms attached through a nitrogen atom linkage.

The term small alkyl is intended to indicate those alkyls with C1 to C6 carbon atoms, either branched or linear in connection.

The term halo as used herein, represents fluoro, chloro, bromo or iodo.

The term aryl refers to aromatic rings e.g., phenyl, substituted phenyl and the like groups as well as rings which are fused e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with 1-3 groups such as alkyl, halo, carboxyalkyl, alkylamino, dialkylamino, alkoxy, alkoxyamino and the like.

The term heteroaryl refers to a monocyclic aromatic hydrocarbon group having 5 or 6 ring atoms, or a bicyclic aromatic group having 8 to 10 atoms, containing at least one heteroatom, O, S, or N, in which a carbon or nitrogen atom is the point of attachment, and in which one additional carbon atom is optionally replaced by a heteroatom selected from O or S, an in which from 1 to 3 additional carbon atoms are optionally replaced by nitrogen heteroatoms. The heteroaryl group is optionally substituted with up to three groups. Heteroaryl thus includes aromatic and partially aromatic groups which contain one or more heteroatoms. Examples of this type are pyrrol, pyridine, oxazole, thiazole and oxazine. Additional nitrogen atoms may be present together with the first nitrogen and oxygen or sulfur, giveing e.g., thiadizaole.

A preferred embodiment of the novel compounds of this invention is realized when:

$R_2$–$R_9$ are independently H, alkyl, or halo;

$Y_1$ is H, alkyl, or halo;

$Y_2$ is 5-pyrimidinyl, 3-pyridyl, or 1-methyl-5-imidazolyl;

$R_1$ is alkyl, alkoxy, phenyl, 5-pyrimidinyl, 3-pyridyl, or 1-methyl-5-imidazolyl; and $X_1$ is N.

The pharmaceutically acceptable salts of the compounds of formula I include the conventional non-toxic salts or the quartemary ammonium salts of the compounds of formula I formed e.g. from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The compounds of the present invention may have asymmetric centers and occur as racemates, racemic mixtures, and as individual diastereomers, with all possible isomers, including optical isomers, being included in the present invention.

Examples of the novel compounds of this invention are as follows:

(3"S,4"R,1'"R and 3"R,4"S,1'"R) 1,3-Dihydro-1-{1'-[1"-(1'"-(5'"-pyrimidinyl)-1'"-ethyl)-3"-methylpiperidin-4"-yl]-piperidin-4'-yl }-2H-benzimidazol-2-one;

(3'R,4'R,1"R and 3'S,4'S,1"R) 1,3-Dihydro-1-{1'-[1"-(1'"-(5""-pyrimidinyl)-1'"-ethyl)-piperidin-4"-yl]-3'-methylpiperidin-4'-yl }-2H-benzimidazol-2-one;

(3'S,4'R,1"R and 3'R,4'S,1"R) 1,3-Dihydro-1-{1'-[1"-(1'"-(5""-pyrimidinyl)-1'"-ethyl)-piperidin-4"-yl]-3'-methylpiperidin-4'-yl}-2H-benzimidazol-2-one;

(3'R,4'R, 1'"R and 3'S,4'S,1'"R) 1,3-Dihydro-1-{1'-[1"-(1'"-(5""-pyrimidinyl)-1'"-ethyl)-piperidin-4"-yl]-3'-ethoxycarbonylpiperidin-4'-yl}-2H-benzimidazol-2-one;

(3'S,4'R,1'"R and 3'R,4'S,1'"R) 1,3-Dihydro-1-{1'-[1"-(1'"-(5""-pyrimidinyl)-1'"-ethyl)-piperidin-4"-yl]-3'-ethoxycarbonylpiperidin-4'-yl}-2H-benzimidazol-2-one;

(2"R,4"S, 1'"R and 2"R,4"R,1'"R) 1,3-Dihydro-1-{1'-[1"-(1'"-(5""-pyrimidinyl)-1'"-ethyl)-2"-methyl-piperidin-4"-yl]-piperidin-4'-yl}-2H-benzimidazol-2-one;

(2"S,4"S, 1'"R) 1 ,3-Dihydro-1-{1'-[1"-(1'"-(5""-pyrimidinyl)-1'"ethyl)-2"-methyl-piperidin-4"-yl]-piperidin-4'-yl}-2H-benzimidazol-2-one;

(2"S,4"R,1'"R) 1,3-Dihydro-1-{1'-[1"-(1'"-(5""-pyrimidinyl)-1'"-ethyl)-2"-methyl-piperidin-4"-yl]-piperidin-4'-yl}-2H-benzimidazol-2-one;

(3'S,4'R, 1'"S and 3'R,4'S,1'"S) 1,3-Dihydro-1-{1'-[1"-(1'"-phenylethyl)-piperidin-4"-yl]-3'-ethoxycarbonylpiperidin-4'-yl}-2H-benaimidazol-2-one;

(3"S,4"R,1'"R) 1,3-Dihydro-1-{1'-[1"-(1'"-(5""-pyrimidinyl)-1'"-ethyl)-3"-methylpiperidin-4"-yl]-piperidin-4'-yl}-2H-benzimidazol-2-one;

(3"R,4"S,1'"R) 1,3-Dihydro-1-{1'-[1"-(1'"-(5""-pyrimidinyl)-1'"-ethyl)-3"-methylpiperidin-4"-yl]-piperidin-4'-yl}-2H-benzimidazol-2-one;

1,3-Dihydro-1-{1'-[1"-(3'"-pyridinecarbonyl)-2"-methyl-piperidin-4"-yl]-piperidin-4'-yl}-2H-benzimidazol-2-one;

(1'"R) 1,3-dihydro-1-{1'-[8"-(1'"-(5""-pyrimidinyl)-1'"-ethyl)piperidin-4"-yl]-8-azabicyclo[3.2.1]octan-3α-yl}-2H-benaimidazol-2-one;

(1'"R) 1,3-dihydro-1-{1'-[8"-(1'"-(5""-pyrimidinyl)-1'"-ethyl)piperidin-4"-yl]-8-azabicyclo[3.2.1]octan-3β-yl}-2H-benaimidazol-2-one;

1,3-Dihydro-1-{1'-[1"-(1'"-methylimidazol-5'"-carbonyl)-piperidin-4"-yl]-piperidin-4'-yl}-2H-benzimidazol-2-one; and 1,3-Dihydro-1-{1'-[1"-(1'"-methylimidazol-5'"-ylcarbonyl)-2"-methyl-piperidin-4"-yl]-piperidin-4'-yl}-2H-benzimidazol-2-one.

The novel compounds of this invention are prepared by the following non-limiting procedures:

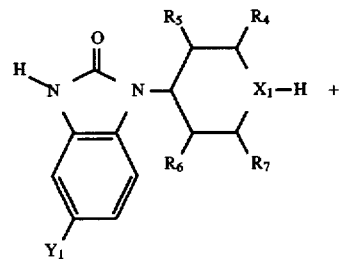

II

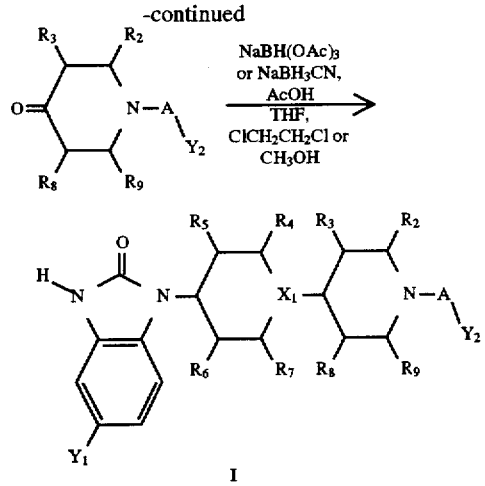

I wherein R2–R9, Y1, Y2, X1 and A are described herein.

The reaction is preferably carried out at room temperature (20°–30° C.) at a pH in the range of 2–7 (acidic) by the addition of glacial acetic acid or hydrochloric acid. A suitably protected 4-piperidone such as A—Y$_2$=CO$_2$Et, CO$_2$CH$_2$Ph, or CO$_2$C(CH$_3$)$_3$ can be used as an intermediate. Deprotection by the usual methods (hydrogenation or acidic hydrolysis followed by basification) provides the free amine compound which can be acylated or alkylated by standard procedures. By this route the most preferred compounds can be obtained after isolation and purification.

The starting materials are either commercially available or can be obtained by conventional procedures such as those described in the Examples section.

The selectivity of the compounds can be measured by radioligand displacement from m1–m5 receptors expressed in chinese hamster ovary cells (CHO) as described in the Examples section. The functional activity of the compounds can be assessed by measuring the agonist induced contractile response on muscle tissue from rabbit vas deferens (M1), the guinea pig left atria (M2), or the guinea pig ileum (M3) as described in the Examples section. The functional activity at the human muscarinic receptors can be assessed by measuring agonist induced phosphoinositide hydrolysis in CHO cells expressing the human m1 and m3 receptors or agonist inhibition of foskolin-stimulated adenylate cyclase activity in CHO cells expressing the human m2 receptor as described in the Examples section.

The instant compounds of this invention are useful in treating and/or preventing the development of myopia. Therapy to inhibit axial-elongation myopia during maturation can be administered by the use of the agent in eye drops. Indeed, in the vast majority of cases, treatment agents are administered to human eyes by the application of eye drops. Eye drops are typically made up at a concentration of active agent between about 0.1 and 4% in the ophthalmic medium. A 0.5%–2% solution of the instant muscarinic antagonist in water would be a likely concentration for clinical use. A pH of about 4.5 to about 7.5 is expected to be acceptable as an ophthalmic drop and practical in terms of known solubility and stability of piperidines. Phosphate buffering is also common for eye drops and is compatible with the instant muscarinic antagonist. A common regimen for application of eye drops is one to three times a day spaced evenly throughout waking hours. More effective agents may require fewer applications or enable the use of more dilute solutions. Alternatively, ointments and solid inserts are now coming into increased use in clinical practice. These aid the ocular penetration of the drug. It is, of course, also possible to administer the above-described active agents in therapeutically effective amounts and dosages in pills, capsules, or other preparations of systemic administration.

In experiments in animals where axial myopia has been experimentally induced by depriving the retina of formed images, it has been noted that amblyopia was also experimentally and coincidentally induced in primates. Amblyopia is evidenced by poor visual acuity in the eye resulting in poor visual performance. Normally, visual acuity improves during maturation. It is known that amblyopia may occur in humans from unknown causes or as part of strabismus. Accordingly, it is expected that administration of therapeutically effective amounts and dosages of the instant muscarinic antagonist might prevent or inhibit the development of permanent or persistent amblyopia in maturing humans with decreased likelihood of sensitization of the eye. It is also expected that humans who have already developed amblyopia from other or even unknown causes might be aided by similar therapeutic treatment with the aforementioned agents.

The following examples are provided in order that this invention might be more fully understood; they are not to be construed as limitative of the invention. The compounds are characterized analytically using techniques such as nuclear magnetic resonance, mass spectrometry, chromatography and the like.

EXAMPLE 1

1-(1S-(5-Pyrimidinyl)-ethyl)-4-oxopiperidine

To a stirred mixture of 2.3 g of (S)-(-)-5-(1-aminoethyl) pyrimidine (O. Cervinska and P. Malon, *Coll. Czechoslov. Chem. Commun.* 1977, 42, 3464–72.), 20 mL of ethanol and 2.0 g of $K_2CO_3$ heated to reflux was added dropwise over 30 min, a solution of 6.2 g of 1-methyl-1-ethyl-4-oxopiperidinium iodide in 110 mL of water. When the addition was complete, the mixture was heated under reflux for an additional 1 h, cooled, basified to pH 9 with $K_2CO_3$ and extracted with 5 times with 50 mL portions of chloroform. The combined organic extracts were dried over $MgSO_4$ and concentrated under reduced pressure. Chromatography over silica gel, eluting with 1:1 tetrahydrofuran:ethyl acetate gave 3.8 g of 1-(1S-(5-pyrimidinyl)-ethyl)-4-oxopiperidine as an oil: $^1H$ NMR (400 MHz, $CDCl_3$) 9.14 (s, 1H), 8.78 (s, 2H), 3.8 (q, J=7 Hz, 1H), 2.7–2.9 (m, 4H), 2.45 (m, 4H), 1.5 (d, J=7 Hz, 3H).

EXAMPLE 2

1-(1R-(5-Pyrimidinyl)-ethyl)-4-oxopiperidine

To a stirred mixture of 2.3 g of (R)-(+)-5-(1-aminoethyl) pyrimidine (O. Cervinska and P. Malon, *Coll. Czechoslov. Chem. Commun.* 1977, 42, 3464–72.), 20 mL of ethanol and 2.0 g of $K_2CO_3$ heated to reflux was added dropwise over 30 min, a solution of 6.2 g of 1-methyl-1-ethyl-4-oxopiperidinium iodide in 110 mL of water. When the addition was complete, the mixture was heated under reflux for an additional 1 h, cooled, basified to pH 9 with $K_2CO_3$ and extracted 5 times with 50 mL portions of chloroform. The combined organic extracts were dried over $MgSO_4$ and concentrated under reduced pressure. Chromatography over silica gel, eluting with 1:1 tetrahydrofuran:ethyl acetate gave 3.8 g of 1-(1R-(5-pyrimidinyl)-ethyl)-4-oxopiperidine as an oil: $^1H$ NMR (400 MHz, $CDCl_3$) 9.14 (s, 1H), 8.78 (s, 2H), 3.8 (q, J=7 Hz, 1H), 2.7–2.9 (m, 4H), 2.45 (m, 4H), 1.5 (d, J=7 Hz, 3H).

EXAMPLE 3

1-(1R-(5-Pyrimidinyl)-ethyl)-3-methyl-4-oxopiperidine

Step 1

A mixture of 10 g of 1-benzyl-3-methyl-4-oxopiperidine and 8 mL of methyl iodide in 100 mL of acetone was stirred at 25° to 30° C. for 6 days then concentrated under reduced pressure to dryness. Drying under vacuum overnight gave 17 g of 1-methyl-1-benzyl-3-methyl-4-oxopiperidinium iodide as a beige foam.

Step 2

To a stirred mixture of 0.9 g of (R)-(+)-5-(1-aminoethyl) pyrimidine (O. Cervinska and P. Malon, *Coll. Czechoslov. Chem. Commun.* 1977, 42, 3464–72.), 35 mL of ethanol and 1 g of $K_2CO_3$ heated to reflux was added dropwise over 30 min, a solution of 4 g of 1-methyl-1-benzyl-3-methyl-4-oxopiperidinium iodide in 60 mL of water. When the addition was complete, the mixture was heated under reflux for an additional 1 h, cooled, and extracted 3 times with 100 mL portions of chloroform. The combined organic extracts were dried over $MgSO_4$ and concentrated under reduced pressure. Chromatography over silica gel, eluting with 90:10 ethyl acetate:tetrahydrofuran gave 1.45 g of 1-(1R-(5-pyrimidinyl)-ethyl)-3-methyl-4-oxopiperidine as an oil: $^1H$ NMR (400 MHz, $CDCl_3$) 9.15 (s, 1H), 8.78 (s, 2H), 3.8 (m, 1H), 3.0–3.2 (m, 3H), 2.5 (m, 1H), 2.4 (m, 2H), 2.2 (m, 1H), 1.65 and 1.45 (2 doublets, J=7 Hz, 3H), 1.2 and 0.98 (2 doublets, J=7 Hz, 3H).

EXAMPLE 4 trans-1-(3-Methyl-4-piperidinyl)benzimidazol-2H-one

Step 1

A mixture of 1 g of 1-benzyl-3-methyl-4-oxopiperidine, 1 g of 1,2-phenylenediamine, 10 mL of methanol, 0.32 g of sodium cyanoborohydride and 2 mL of glacial acetic acid was stirred at room temperature for 12 h, basified by addition of 1 mL of 6N sodium hydroxide and concentrated to near dryness under reduced pressure. The residue was partitioned between 100 mL of ethyl acetate and 10 mL of saturated aqueous sodium carbonate and the organic layer dried over $MgSO_4$ and concentrated under reduced pressure. The residue was dissolved in 25 mL of ethyl acetate and stirred with 10 mL of saturated aqueous sodium carbonate in an ice bath while a solution of 10 mL of 1.93M phosgene in toluene was added. The resulting mixture was allowed to warm to room temperature and stirred for 4 h, diluted with 250 mL of ethyl acetate and filtered to remove 2-hydroxybenzimidazole byproduct. The layers were separated and the organic layer dried over $MgSO_4$ and concentrated under reduced pressure. Chromatography over silica gel, eluting with 80:20 ethyl acetate:hexane gave first 0.75 g of cis-1-(1-benzyl-3-methyl-4-piperidinyl) benzimidazol-2H-one as a white solid: $^1H$ NMR (400 MHz, $CDCl_3$) 9.65 (s, 1H), 7.4–7.0 (m, 9H), 4.4 (m, 1H), 3.5 (dd, 2H), 3.1 (m, 2H), 2.8 (d, 1H), 2.38 (d, 1H), 2.3 (br s, 1H), 2.18 (br t, 1H), 1.7 (br m, 1H), 1.2 (d, 3H); followed by 0.25 g of trans-1-(1-benzyl-3-methyl-4-piperidinyl) benzimidazol-2H-one as a white solid in the later fractions: $^1H$ NMR (400 MHz, $CDCl_3$) 11 (s, 1H), 7.4–7.0 (m, 9H), 4.1 (br m, 2H), 3.6 (s, 2H), 3.1 (m, 2H), 2.6 (br m, 2H), 2.3 (br t, 1H), 1.95 (br t, 1H), 1.85 (br d, 1H), 0.76 (d, 3H).

Step 2

A mixture of 200 mg of trans-1-(1-benzyl-3-methyl-4-piperidinyl) benzimidazol-2H-one, 100 mL of absolute methanol, 0.5 mL of 2N ethanolic HCl and 100 mg of 20% palladium hydroxide on carbon was shaken under 55 psi of hydrogen for 3 days, then filtered and concentrated to dryness under reduced pressure. The residue was partitioned between 5×50 mL portions of chloroform and 5 mL of 2N sodium hydroxide. The combined organic extracts were dried over $MgSO_4$ and concentrated under reduced pressure. Trituration with 10 mL of ethyl acetate gave 150 mg of trans-1-(3-methyl-4-piperidinyl) benzimidazol-2H-one as a white solid. $^1$H NMR (400 MHz, $CDCl_3$) 9.2 (br s, 1H), 7.3 (m, 1H), 7.1 (m, 3H), 4.1 (br m, 1H), 3.3 (m, 2H), 2.9 (t, 1H), 2.5 (m, 1H), 2.4 (m, 1H), 1.7–1.9 (br m, 2H), 1.8 (d, 3H).

EXAMPLE 5

(3'R,4'R,1'''R and 3'S,4'S,1'''R) 1,3-Dihydro-1-{1'-[1''-(1'''-(5''''-pyrimidinyl)-1'''-ethyl)-piperidin-4''-yl]-3'-methylpiperidin-4'-yl }-2H-benzimidazol-2-one A mixture of 0.20 g of 1-(1R-(5-pyrimidinyl)-ethyl)-4-oxopiperidine, 0.15 g of trans-1-(3-methyl-4-piperidinyl) benzimidazol-2H-one, 10 mL of 1,2-dichloroethane, 0.3 mL of glacial acetic acid and 0.5 g of sodium triacetoxyborohydride was stirred at room temperature for 48 h. The reaction mixture was poured into 100 mL chloroform and 25 mL saturated aqueous $Na_2CO_3$ and the layers separated. The aqueous layer was extracted with 2×25 mL of chloroform and the combined organic layers dried over $MgSO_4$ and concentrated under reduced pressure. Purification of the residue by preparative thin chromatography on silica gel eluting with 430:50:20 $CHCl_3$: MeOH:conc. $NH_4OH$ followed by trituration with 10 mL of ethyl acetate gave 90 mg of (3'R,4'R,1'''R and 3'S,4'S,1'''R) 1,3-dihydro-1-{1'-[1''-(1'''-(5''''-pyrimidinyl)-1'''-ethyl)-piperidin-4''-yl]-3'-methylpiperidin-4'-yl}-2H-benzimidazol-2-one as a white solid. $^1$H NMR (400 MHz, $CDCl_3$) 10.9 (s, 1H), 9.15 (s, 1H), 8.7 (s, 2H), 7.26 (br m, 1H), 7.0–7.1 (br m, 3H), 4.05 (br m, 1H), 3.6 (q, J=7 Hz, 1H), 3.0–3.2 (m, 3H), 2.7 (m, 1H), 2.6–2.3 (m, 4H), 2.1–2.0 (m, 3H), 1.9–1.8 (br m, 3H), 1.6 (br m, 2H), 1.4 (d, J=7 Hz, 3H), 0.76 (d, J=7 Hz, 3H). The citrate salt crystallized from ethyl acetate/methanol: Analysis calculated for $C_{24}H_{32}N_6O.1.0H_2O.1.5\ C_6H_8O_7$: C: 54.53, H: 6.38, N: 11.56; found C: 54.85, H: 6.38, N: 11.56.

EXAMPLE 6

(3''S,4''R,1'''R) 1,3-Dihydro-1-{1'-[1''-(5''''-pyrimidinyl)-1'''-ethyl)-3''-methylpiperidin-4''-yl]-piperidin-4'-yl}-2H-benzimidazol-2-one and (3''R,4''S,1'''R) 1,3-dihydro-1-{1'-[1''-(1'''-(5''''-pyrimidinyl)-1'''-ethyl)-3 ''-methylpiperidin-4''-yl]-piperidin-4'-yl}-2H-benzimidazol-2-one A mixture of 1.2 g of 1-(1R-(5-pyrimidinyl)-ethyl)-3-methyl-4-oxopiperidine, 2.0 g of 1-(4-piperidinyl) benzimidazol-2H-one, 40 mL of 1,2-dichloroethane, 0.6 mL of glacial acetic acid, 2 g of powdered activated 4Å molecular sieves was stirred at 80° C. for 30 min, then at 40° C. for 1 h, and cool to room temperature over 1 h. To this mixture was added 3.0 g of sodium triacetoxyborohydride. Stirring was continued at room temperature for 48 h. The reaction mixture was poured into 100 mL chloroform and 25 mL saturated aqueous $Na_2CO_3$ and the layers separated. The aqueous layer was extracted with 2×100 mL of chloroform and the combined organic layers dried over $MgSO_4$ and concentrated under reduced pressure. Purification of the residue by low pressure chromatography eluting with 85:15 $CH_2Cl_2$:MeOH, followed by preparative thin chromatography on silica gel eluting with 210:40:15 $CHCl_3$:MeOH:conc. $NH_4OH$ followed by trituration with 10 mL of ethyl acetate gave 540 mg of (3''S,4''R,1'''R and 3''R,4''S,1'''R) 1,3-dihydro-1-{1'-[1''-(1'''-(5''''-pyrimidinyl)-1'''-ethyl)-3''-methylpiperidin-4''-yl]-piperidin-4'-yl }-2H-benzimidazol-2-one as a gum: $^1$H NMR (400 Mhz, $CDCl_3$) 9.4 (s, 1H), 9.1 (s, 1H), 8.71 (2 singlets, 2H), 7.3 (br m, 1H), 7.05 (br m, 3H), 4.4 (br m, 1H), 3.52 and 3.45 (2 quartets, J=7 Hz, 1H), 3.3–3.2 (m, 2H), 3.0 (m, 1H), 2.8–2.7 (m, 1H), 2.5–2.3 (m, 3H), 2.2–1.9 (br m, 5H), 1.8 (br m, 3H), 1.8–1.5 (br m, 1H), 1.35 (t, 3H), 1.06 (t, 3H). The citrate salt precipitated from ethyl acetate/methanol: Analysis calculated for $C_{24}H_{32}N_6O.0.5\ H_2O.1.5C_6H_8O_7$: C: 55.22, H: 6.32, N: 11.71; found C: 55.45, H: 6.44, N: 11.77.

Preparative HPLC on C-1 8 column (Deltapak, C-18 eluting with a gradient of 0:100 to 100:0 of acetonitrile: 0.1% ammonium bicarbonate gave first 0.20 g of (3''R,4''S,1'''R) 1,3-dihydro-1-{1'-[1''-(1'''-(5''''-pyrimidinyl)-1'''-ethyl)-3''-methylpiperidin-4''-yl]-piperidin-4'-yl}-2H-benzimidazol-2-one: $[\alpha]_D$=+23.5° (c=0.575, MeOH); mp 116–118° C.; $^1$H NMR (400 Mhz, $CDCl_3$) 9.15 (s, 1H), 9.05 (br s, 1H), 8.7 (s, 2H), 7.3 (br m, 1H), 7.05 (br m, 3H), 4.4 (br m, 1H), 3.45 (q, 1H), 3.25 (m, 2H), 3.0 (m, 1H), 2.6 (d, 1H), 2.5 (m, 2H), 2.2–1.9 (br m, 5H), 1.85 (br m, 3H), 1.65 (br m, 2H), 1.38 (d, 3H), 1.07 (d, 3H); followed by (3''R,4''S,1'''R) 1,3-dihydro-1-{1'-[1''-(1'''-(5''''-pyrimidinyl)-1'''-ethyl)-3''-methylpiperidin-4''-yl]-piperidin-4'-yl}-2H-benzimidazol-2-one: $[\alpha]_D$=−26.0° (c=0.575, MeOH); mp 113°–115° C.; $^1$H NMR (400 Mhz, $CDCl_3$) 9.15 (s, 1H), 8.73 (s, 2H), 8.62 (br s, 1H), 7.3 (br m, 1H), 7.05 (br m, 3H), 4.4 (br m, 1H), 3.55 (q, 1H), 3.25 (m, 2H), 2.8 (m, 1H), 2.4 (m, 2H), 2.2–1.9 (br m, 6H), 1.85 (br d, 1H), 1.65 (br m, 4H), 1.36 (d, 3H), 1.08 (d, 3H).

EXAMPLE 7

(3'S,4'R,1'''R and 3'R,4'S,1'''R) 1,3-Dihydro-1-{1'-[1''-(1'''-(5''''-pyrimidinyl)-1'''-ethyl)-piperidin-4''-yl]-3'-methylpiperidin-4'-yl}-2H-benzimidazol-2-one Step 1

A mixture of 660 mg of cis-1-(1-benzyl-3-methyl-4-piperidinyl) benzimidazol-2H-one (a product of Step 1, Example 4), 100 mL of absolute methanol, 2 mL of 2N ethanolic HCl and 400 mg of 20% palladium hydroxide on carbon was shaken under 55 psi of hydrogen for 3 days, then filtered and concentrated to dryness under reduced pressure. The residue was partitioned between 5×50 mL portions of chloroform and 5 mL of 2N sodium hydroxide. The combined organic extracts were dried over $MgSO_4$ and concentrated under reduced pressure. Trituration with 10 mL of ethyl acetate gave 500 mg of cis-1-(3-methyl-4-piperidinyl) benzimidazol-2H-one as a white solid. $^1$H NMR (400 MHz, $CDCl_3$) 9.2 (br s, 1H), 7.2 (m, 1H), 7.05 (m, 3H), 4.48 (dt, 1H), 3.3 (d, 2H), 3.06 (dd, 1H), 3.0–2.85 (complex m, 2H), 2.78 (dt, 1H), 1.8 (br dd, 1H), 1.68 (br, 1H), 1.12 (d, 3H).

Step 2

A mixture of 0.25 g of 1-(1R-(5-pyrimidinyl)-ethyl)-4-oxopiperidine, 0.20 g of cis-1-(3-methyl-4-piperidinyl) benzimidazol-2H-one, 10 mL of 1,2-dichloroethane, 0.3 mL of glacial acetic acid and 0.5 g of sodium triacetoxyborohydride was stirred at room temperature for 48 h. The reaction mixture was poured into 100 mL chloroform and 25 mL saturated aqueous $Na_2CO_3$ and the layers separated. The aqueous layer was extracted with 2×25 mL of chloroform and the combined organic layers dried over $MgSO_4$ and concentrated under reduced pressure. Purification of the residue by preparative thin chromatography on silica gel eluting with 430:50:20 $CHCl_3$: MeOH:conc. $NH_4OH$ followed by trituration with 10 mL of ethyl acetate gave 450 mg of (3'S,4'R,1"'R and 3'R,4'S,1"'R) 1,3-dihydro- 1-{1'-[1"-(1"'-(5""-pyrimidinyl)-1"'-ethyl)-piperidin-4"-yl]-3'-methylpiperidin-4'-yl}-2H-benzimidazol-2-one as a white solid: $^1$H NMR (400 MHz, CDCl$_3$) 10.7 (br s, 1H), 9.15 (s, 1H), 8.7 (s, 2H), 7.2 (m, 1H), 7.1 (m, 2H), 7.0 (m, 2H), 4.45 (dt, 1H), 3.58 (q, J=7 Hz, 1H), 3.1–2.75 (m, 5H), 2.6 (d, 1H), 2.4–2.2 (m, 4H), 2.0 (m, 2H), 1.85–1.5 (br m, 4H), 1.4 (d, J=7 Hz, 3H), 1.1 (d, J=7 Hz, 3H). The citrate salt crystallized from ethyl acetate/methanol: Analysis calculated for C$_{24}$H$_{32}$N$_6$O.1.0CH$_3$CO$_2$CH$_2$CH$_3$.1.3C$_6$H$_8$O$_7$: C: 56.69, H: 6.70, N: 11.08; found C: 56.40, H: 6.77, N: 11.35.

EXAMPLE 8

(±)-2-Methyl-4-oxo-1-propyl piperidine

Step 1

A mixture of 6 g of methyl acetoacetate, 5 mL of 1-propylamine, 40 mL of 1,2-dichloroethane, 3 mL of glacial acetic acid and 16 g of sodium triacetoxyborohydride was stirred at room temperature for 4 days. The reaction mixture was poured into 200 mL chloroform and 50 mL saturated aqueous Na$_2$CO$_3$ and the layers separated. The aqueous layer was extracted with 200 mL of chloroform and the combined organic layers dried over MgSO$_4$ and concentrated under reduced pressure. After drying under vacuum, 9 g of (±)-methyl 2-(1-propylamino)butyrate was obtained as an oil: TLC (EtOAc); $^1$H NMR (400 MHz, CDCl$_3$) 6.2 (br s, 1H), 3.65 (s, 3H), 3.2 (complex m, 2H), 2.65 (complex m, 2H), 2.45 (dd, 1H), 1.55 (m, 2H), 1.4 (d, 3H), 0.95 (t, 3H).

Step 2

A mixture of 9 g of (±)-methyl 2-(1-propylamino) butyrate, 100 mL of anhydrous methanol and 10 mL of methyl acrylate was kept at room temperature in a stoppered flask for 3 days. The mixture was then concentrated under reduced pressure and purified by evaporative distillation. The colorless distillate, 10.5 g, obtained at oven temperature 90°–95° C., 1 mm, was (±)-methyl 2-(2-methoxycarbonylethyl(1-propyl)amino)butyrate: TLC (EtOAc); $^1$H NMR (400 MHz, CDCl$_3$) 3.66 (s, 3H), 3.64 (s, 3H), 2.8–2.2 (complex m, 6H), 1.45 (complex m, 2H), 1.0 (d, 3H), 0.85 (t, 3H).

Step 3

To a stirred solution of 162 mL of 0.5M potassium bistrimethylsilylamide in toluene and 600 mL of anhydrous tetrahydrofuran cooled to –78° C. under nitrogen atmosphere was added dropwise a solution of 7.5 g of (±)-methyl 2-(2-methoxycarbonylethyl(1-propyl)amino)butyrate in 50 mL of dry (tetrahydrofuran over 20 min, keeping the internal temperature under –70° C. The mixture was allowed to warm to –20° C. for 2 h, then quenched with 100 mL of saturated aqueous sodium bicarbonate and extracted into 3×200 mL portions of ethyl acetate. The combined extracts were dried over MgSO$_4$ and concentrated under reduced pressure. There was obtained 6.6 g of predominantly (±)-trans-5-carbomethoxy-2-methyl-4-oxo-1-propyl piperidine as an oil: TLC (EtOAc); $^1$H NMR (400 MHz, CDCl$_3$) 3.76 (s, 3H), 3.2 (m, 1H), 2.9 (m, 1H), 2.62–2.0 (complex m, 6H), 1.5 (m, 2H), 1.25 (d, 3H), 0.5 (dd, 3H).

Step 4

A solution of 6.5 g of predominantly (±)-trans-5-carbomethoxy-2-methyl-4-oxo-1-propyl piperidine and 30 mL of 20% hydrochloric acid was heated to reflux for 2 h. The solution was cooled in an ice bath, basified by addition of NaOH pellets until the pH was 9–10 and extracted with 5×100 mL of chloroform. The combined organic extracts were dried over MgSO$_4$ and concentrated under reduced pressure. After azeotropic drying with toluene there was obtained 5.6 g of predominantly (±)-2-methyl-4-oxo-1-propyl piperidine as an amber oil: TLC (EtOAc); $^1$H NMR (400 MHz, CDCl$_3$) 3.1 (m, 1H), 2.9 (m, 1H), 2.8–2.6 (complex m, 3H), 2.5 (m, 4H), 1.5 (m, 2H), 1.15 (d, 3H), 0.9 (t, 3H).

EXAMPLE 9

1-(1R-(5-Pyrimidinyl)-ethyl)-2R-methyl-4-oxopiperidine and 1-(1R-(5-Pyrimidinyl)-ethyl)-2S-methyl-4-oxopiperidine Step 1

A mixture of 5.6 g of predominantly (±)-2-methyl-4-oxo-1-propyl piperidine, 250 mL of acetone and 5 mL of iodomethane was stirred at room temperature for 48 h. The mixture was filtered and concentrated under reduced pressure. After drying under vacuum there was obtained 6 g of (±)-2-methyl-4-oxo-1-methyl-1-propyl-piperidinium iodide as a brown gum (mixture of diastereomers).

Step 2

To a stirred mixture of 0.25 g of (R)-(+)- 5-(1-aminoethyl) pyrimidine (O. Cervinska and P. Malon, Coll. Czechoslov. Chem. Commun. 1977, 42, 3464–72.), 10 mL of ethanol and 0.3 g of K$_2$CO$_3$ heated to reflux was added dropwise over 30 min, a solution of 1.2 g of (±)-2-methyl-4-oxo-1-methyl-1-propyl-piperidinium iodide in 25 mL of water. When the addition was complete, the mixture was heated under reflux for an additional 1 h, cooled, and extracted 3 times with 100 mL portions of chloroform. The combined organic extracts were dried over MgSO$_4$ and concentrated under reduced pressure. Chromatography over silica gel, eluting with a gradient of 95:5 to 80:20 ethyl acetate:tetrahydrofuran gave first 150 mg of 1-(1R-(5-pyrimidinyl)-ethyl)-2R-methyl-4-oxopiperidine as an oil: $^1$H NMR (400 MHz, CDCl$_3$) 9.18 (s, 1H), 8.8 (s, 2H), 4.2 (dd, 1H), 3.3 (dd, 1H), 3.2 (dd, 2H), 2.7 (m, 1H), 2.6 (m, 1H), 2.3 (m, 1H), 1.4 (d, 3H) and 1.2 (d, 3H); followed by 200 mg of 1-(1R-(5-pyrimidinyl)-ethyl)-2S-methyl-4-oxopoxopiperidine as an oil: $^1$H NMR (400 MHz, CDCl$_3$) 9.18 (s,1H), 8.78 (s, 2H), 4.2–4.0 (complex m, 3H), 3.08–0.9 (complex m, 3H), 2.6 (m, 1H), 2.4–2.2 (m, 1H), 1.5 (d, 3H) and 1.1 (d, 3H).

EXAMPLE 10

(2"R,4"S,1"'R and 2"R,4"R,1"'R) 1,3-Dihydro-1-{1'-[1"-(1"'-(5""-pyrimidinyl)-1"'-ethyl)-2"-methylpiperidin-4"-yl]-piperidin-4'-yl}-2H-benzimidazol-2-one A mixture of 0.20 g of 1-(1R-(5-pyrimidinyl)-ethyl)-2R-methyl-4-oxopiperidine, 0.450 g of 1-(4-piperidinyl) benzimidazol-2H-one, 8 mL of 1,2-dichloroethane, 0.2 mL of glacial acetic acid and 0.40 g of sodium triacetoxyborohydride was stirred at room temperature for 48 h. The reaction mixture was poured into 100 mL chloroform and 25 mL saturated aqueous Na$_2$CO$_3$ and the layers separated. The aqueous layer was extracted with 2×25 mL of chloroform and the combined organic layers dried over MgSO$_4$ and concentrated under reduced pressure. Purification of the residue by preparative thin chromatography on silica gel eluting with 80:20 CH$_2$Cl$_2$:MeOH followed by trituration with 10 mL of ethyl acetate gave 120 mg of(2"R,4"S,1"'R and 2"R,4"R,1"'R) 1,3-dihydro-1-{1'-[1"-(1"'-(5""-pyrimidinyl)-1"'-ethyl)-2"-methylpiperidin-4"-yl]-piperidin-4'-yl}-2H-benzimidazol-2-one as a gum: $^1$H NMR (400 MHz, CDCl$_3$) 10.6 (br s, 1H), 9.5 and 9.06 (2 s, 1H), 8.8 and 8.7 (2 s, 2H), 7.3 (br m, 1H), 7.05 (br m, 3H), 4.4(br m, 1H), 3.6 and 3.5 (2 quartets, 1H), 3.1 (m, 1H), 2.7 (m, 1H), 2.45 (m, 4H), 2.2 (m, 1H), 1.8 (br m, 5H), 1.25 (br m, 3H), 1.8–1.5 (complex m, 7H). The citrate salt precipitated from ethyl acetate/methanol: Analysis calculated for $C_{24}H_{32}N_6O.1.0\ CH_3CO_2CH_2CH_3.1.2C_6H_8O_7$: C: 57.19, H: 6.76, N: 11.37; found C: 57.21, H: 6.93, N: 11.64.

EXAMPLE 11

(2"S,4"S,1"'R) 1,3-Dihydro-1-{1'-[1"-(1"'-(5""-pyrimidinyl)-1"'-ethyl)-2"-methyl-piperidin-4"-yl]-piperidin-4'-yl}-2H-benzimidazol-2-one and (2"S, 4"R,1"'R) 1,3-dihydro-1-{1'-[1"-(1"'-(5""-pyrimidinyl)-1"'-ethyl)-2"-methyl-piperidin-4"-yl]-piperidin-4'-yl}-2H-benzimidazol-2-one A mixture of 0.20 g of 1-(1R-(5-pyrimidinyl)-ethyl)-2R-methyl-4-oxopiperdine, 0.450 g of 1-(4-piperidinyl) benzimidazol-2H-one, 8 mL of 1,2-dichloroethane, 0.2 mL of glacial acetic acid and 0.40 g of sodium triacetoxyborohydride was stirred at room temperature for 48 h. The reaction mixture was poured into 100 mL chloroform and 25 mL saturated aqueous $Na_2CO_3$ and the layers separated. The aqueous layer was extracted with 2×25 mL of chloroform and the combined organic layers dried over $MgSO_4$ and concentrated under reduced pressure. Purification of the residue by preparative thin chromatography on silica gel eluting with 425:50:25 $CHCl_3$:MeOH:$NH_4OH$ gave product contaminated with 1-(1R-(5-pyrimidinyl)-ethyl)-2R-methyl-4-hydroxypiperidine formed by reduction of the piperidone. Further purification by preparative thin chromatography on silica gel eluting twice with 375:100:25 tetrahydrofuran: $CH_2Cl_2$:MeOH gave the pure product diastereomers in two bands. The upper band gave 20 mg of (2"S,4"S,1"'R) 1,3-dihydro- 1-{1'-[1"-(1"'-(5""-pyrimidinyl) -1"'-ethyl)-2"-methyl-piperidin-4"-yl]-piperidin-4'-yl}-2H-benzimidazol-2-one after trituration with 10 mL of ethyl ether: $^1$H NMR (400 MHz, $CDCl_3$) 10.0 (br s, 1H), 9.1 (s, 1H), 8.75 (s, 2H), 7.3 (br m, 1H), 7.05 (m, 3H), 4.4(br m, 1H), 3.75 (q, 1H), 3.2–2.9 (m, 3H), 2.8–2.1 (m, 6H), 1.9 (br d, 2H), 1.8–1.4 (complex m, 2H), 1.4 (d, 3H), 1.3–1.1 (complex m, 3H), 1.0 (d, 3H); The citrate salt precipitated from ethyl acetate/methanol: Analysis calculated for $C_{24}H_{32}N_6O.1.0CH_3CO_2CH_2CH_3.1.0C_6H_8O_7$: C: 58.27, H: 6.90, N: 11.99; found C: 58.09, H: 6.92, N: 11.77.

The lower band gave 40 mg of (2"S,4"R,1"'R) 1,3-dihydro-1-{1'-[1"-(1"'-(5""-pyrimidinyl)-1"'-ethyl)-2"-methyl-piperidin-4"-yl]-piperidin-4'-yl}-2H-benzimidazol-2-one after trituration with 10 mL of ethyl ether:$^1$H NMR (400 MHz, $CDCl_3$) 10.3 (br s, 1H), 9.15 (s, 1H), 8.7 (s, 2H), 7.3 (m, 1H), 7.1–7.0 (m, 3H), 4.36 (br q, 2H), 3.15 (m, 3H), 2.6–2.0 (complex m, 6H), 1.9 (m, 4H), 1.55 (d, 3H), 1.4 (br m, 2H), 1.2 (d, 3H). The citrate salt precipitated from ethyl acetate/methanol: Analysis calculated for $C_{24}H_{32}N_6O.0.45CHCl_3.2.0\ C_6H_8O_7$: C: 50.99, H: 5.69, N: 9.79; found C: 50.72, H: 6.07, N: 9.42.

EXAMPLE 12

(±)-cis-1-(3-Ethoxycarbonyl-4-piperidinyl) benzimidazol-2H-one

Step 1

A mixture of 15 g of ethyl 4-oxo-3-piperidine carboxylate hydrochloride, 500 mL of methylene chloride, 16 g of di-tert-butyldicarbonate and 15 mL of triethylamine was stirred for 4 days at room temperature. The resulting mixture was washed with 100 mL of sat'd. sodium carbonate, dried over $MgSO_4$ and concentrated under reduced pressure. Drying under vacuum overnight gave 19 g of ethyl 1-tert-butyloxycarbonyl-4-oxo-3-piperidine carboxylate as a solid: $^1$H NMR (400 MHz, $CDCl_3$) 12 (s, 1H), 4.3 (dd, 2H), 4.1 (s, 2H), 3.6 (m, 2H), 2.4 (m, 2H), 1.5 (s, 9H), 1.3 (t, 3H).

Step 2

A mixture of 4 g of ethyl 1-tert-butyloxycarbonyl-4-oxo-3-piperidine carboxylate, 3 g of 1,2-phenylenediamine, 40 mL of absolute methanol, 1 mL of acetic acid and 1 g of sodium cyanoborohydride was stirred at room temperature overnight. The resulting mixture was concentrated to dryness under reduced pressure and partitioned between 3×200 mL of chloroform and 100 mL of sat'd. sodium carbonate. The combined extracts were dried over $MgSO_4$ and concentrated under reduced pressure. The residue was dissolved in 200 mL of ethyl acetate and stirred with 100 mL of saturated aqueous sodium carbonate in an ice bath while a solution of 10 mL of 1.93M phosgene in toluene was added. The resulting mixture was allowed to warm to room temperature and stirred for 24 h, diluted with 250 mL of ethyl acetate. The layers were separated and the organic layer dried over $MgSO_4$ and concentrated under reduced pressure. Low pressure chromatography over silica gel, eluting with 90:10 ethyl acetate:tetrahydrofuran gave first 0.50 g of (±)-trans --1-(1-tert-butyloxycarbonyl-3-ethoxycarbonyl-4-piperidinyl)benzimidazol-2H-one as a white solid: $^1$H NMR (400 MHz, $CDCl_3$) 9.8 (s, 1H), 7.05 (m, 4H), 4.6–4.2 (br m, 3H), 3.9 (dd, 2H), 3.6 (br m, 2H), 3.0 (br m, 1H), 2.5 (br m, 1H), 1.85 (br d, 1H), 1.5 (s, 9H), 0.95 (t, 3H); followed by 4.6 g of (±)-cis --1-(1-tert-butyloxycarbonyl-3-ethoxycarbonyl-4-piperidinyl) benzimidazol-2H-one as a white solid: $^1$H NMR (400 MHz, $CDCl_3$) 7.05 (m, 4H), 4.6 (br d, 1H), 4.5 (br m, 2H), 3.9 (complex m, 2H), 3.6 (br m, 2H), 3.05 (br m, 1H), 2.95 (br m, 1H), 1.85 (br d, 1H), 1.5 (s, 9H), 0.95(t, 3H). The (±)-cis --1-(1-tert-butyloxycarbonyl-3-ethoxycarbonyl-4-piperidinyl) benzimidazol-2H-one (0.5 g) could be converted into predominantly the more stable (±)-trans --1-(1-tert-butyloxycarbonyl-3-ethoxycarbonyl-4-piperidinyl) benzimidazol-2H-one by stirring for 2 days in 5 mL of ethanol with 325 mg of cesium carbonate at room temperature.

Step 3

To a stirred solution of 1.5 g of (±)-cis --1-(1-tert-butyloxycarbonyl-3-ethoxycarbonyl-4-piperidinyl) benzimidazol-2H-one in 100 mL of ethyl acetate and 25 mL of methylene chloride cooled in an ice bath was added a stream of hydrogen chloride gas for 10 min. The mixture was allowed to warm to room temperature for 5 h, then concentrated to dryness under reduced pressure, and partitioned between sat'd. sodium carbonate and 3×100 mL of chloroform. The combined extracts were dried over $MgSO_4$ and concentrated under reduced pressure. Drying under vacuum gave 0.50 g of (±)-cis-1-(3-ethoxycarbonyl-4-piperidinyl)benzimidazol-2H-one as a foam.

EXAMPLE 13

(3'R,4'R,1"'R and 3'S,4'S,1"'R) 1,3-Dihydro-1-{1'-[1"-(1"'-(5""-pyrimidinyl)-1"'-ethyl)-piperidin-4"-yl]-3'-ethoxycarbonylpiperidin-4'-yl}-2H-benzimidazol-2-one A mixture of 0.450 g of 1-(1R-(5-pyrimidinyl)-ethyl)-2R-methyl-4-oxopiperidine, 0.50 g of (±)-cis-1-(3-ethoxycarbonyl-4-piperidinyl)benzimidazol-2H-one, 20 mL of 1,2-dichloroethane, 0.6 mL of glacial acetic acid and 1.8 g of sodium triacetoxyborohydride was stirred at room temperature for 3 days. The reaction mixture was poured into 100 mL chloroform and 25 mL saturated aqueous $Na_2CO_3$ and the layers separated. The aqueous layer was extracted with 2×50 mL of chloroform and the combined organic layers dried over $MgSO_4$ and concentrated under reduced pressure. Purification of the residue by preparative thin chromatography on silica gel eluting with 400:50:25 $CHCl_3$:MeOH:$NH_4OH$ gave product contaminated with 1-(1R-(5-pyrimidinyl)-ethyl)-2R-methyl-4-hydroxypiperidine formed by reduction of the piperidone. Further purification by preparative thin chromatography on silica gel eluting with 375:100:25 tetrahydrofuran:$CH_2Cl_2$:MeOH gave 0.60 g of (3'R,4'R,1'''R and 3'S,4'S,1'''R) 1,3-dihydro-1-{1'-[1"-(1'''-(5""-pyrimidinyl)-1'''-ethyl)-piperidin-4"-yl]-3'-ethoxycarbonylpiperidin-4'-yl}-2H-benzimidazol-2-one: $^1$H NMR (400 MHz, $CDCl_3$) 9.15 (s, 1H), 8.9 (br s, 1H), 8.7 (s, 2H), 7.5 (br dd, 1H), 7.05 (m, 3H), 4.4 (br m, 1H), 4.05 (m, 1H), 3.9 (m, 1H), 3.56 (br dd, 1H), 3.4 (d, 1H), 3.25–3.0 (complex m, 4H), 2.8 (m, 1H), 2.62 (m, 1H), 2.55 (m, 1H), 2.38 (m, 1H), 2.0 (m, 1H), 1.8–1.4 (complex m, 6H), 1.4 (d, 3H), 1.0 (dt, 3H); The citrate salt precipitated from ethyl acetate/methanol: Analysis calculated for $C_{26}H_{34}N_6O_3 \cdot 1.4 C_6H_8O_7$: C: 55.26, H: 6.09, N: 11.24; found C: 55.19, H: 6.29, N: 11.29.

EXAMPLE 14

(±)-trans-1-(3-Ethoxycarbonyl-4-piperidinyl)benzimidazol-2H-one

To a stirred solution of 1.0 g of (±)-trans-1-(1-tert-butyloxycarbonyl-3-ethoxycarbonyl-4-piperidinyl)benzimidazol-2H-one in 150 mL of ethyl acetate cooled to −78° C. was added a stream of hydrogen chloride gas for 5 min. The mixture was allowed to warm to room temperature for 2 h, then concentrated to dryness under reduced pressure, and partitioned between sat'd. sodium carbonate and 3×100 mL of chloroform. The combined extracts were dried over $MgSO_4$ and concentrated under reduced pressure. Drying under vacuum gave 0.700 g of (±)-trans-1-(3-ethoxycarbonyl-4-piperidinyl)benzimidazol-2H-one as a solid: $^1$H NMR (400 MHz, $CDCl_3$): 11 (br s, 1H), 7.1 (m, 4H), 4.5 (br m, 1H), 3.9 (dd, 2H), 3.6 (br m, 1H), 3.5 (d, 1H), 3.3 (d, 1H), 2.85 (m, 2H), 2.5 (br q, 1H), 1.9 (d, 1H), 0.9 (t, 3H).

EXAMPLE 15

(3'S,4'R,1'''R and 3'R,4'S,1'''R) 1,3-Dihydro-1-{1'-[1"-(1'''-(5""-pyrimidinyl)-1'''-ethyl)-piperidin-4"-yl]-3'-ethoxycarbonylpiperidin-4'-yl}-2H-benzimidazol-2-one A mixture of 0.350 g of 1-(1R-(5-pyrimidinyl)-ethyl)-2R-methyl-4-oxopiperidine, 0.250 g of (±)-trans-1-(3-ethoxycarbonyl-4-piperidinyl)benzimidazol-2H-one, 8 mL of 1,2-dichloroethane, 0.2 mL of glacial acetic acid and 0.8 g of sodium triacetoxyborohydride was stirred at room temperature for 48 h. The reaction mixture was poured into 100 mL chloroform and 25 mL saturated aqueous $Na_2CO_3$ and the layers separated. The aqueous layer was extracted with 2×50 mL of chloroform and the combined organic layers dried over $MgSO_4$ and concentrated under reduced pressure. Purification of the residue by preparative thin chromatography on silica gel eluting with 20:1 THF:$NH_4OH$ gave product contaminated with 1-(1R-(5-pyrimidinyl)-ethyl)-2R-methyl-4-hydroxypiperidine formed by reduction of the piperidone. Further purification by preparative thin chromatography on silica gel eluting with 90:10 $CH_2Cl_2$:MeOH gave 0.24 g of (3'S,4'R,1'''R and 3'R,4'S,1'''R) 1,3-dihydro-1-{1'-[1"-(1'''-(5""-pyrimidinyl)-1'''-ethyl)-piperidin-4"-yl]-3'-ethoxycarbonylpiperidin-4'-yl}-2H-benzimidazol-2-one: $^1$H NMR (400 MHz, $CDCl_3$) 9.15 (s, 1H), 8.7 (s, 2H), 7.5 (br m, 1H), 7.05 (m, 3H), 4.4 (br m, 1H), 3.9 (q, 2H), 3.6 (br m, 2H), 3.2 (d, 1H), 3.05 (br m, 2H), 2.85 (d, 1H), 2.45 (complex m, 4H), 2.55 (t, 1H), 1.8 (m, 1H), 1.6 (m, 6H), 1.4 (2×d, 3H), 0.95 (dt, 3H); The citrate salt precipitated from ethyl acetate/methanol: Analysis calculated for $C_{26}H_{34}N_6O_3 \cdot 1.4 C_6H_8O_7 \cdot 0.4 CH_3CO_2CH_2CH_3$: C: 54.81, H: 6.18, N: 10.48; found C: 55.03, H: 6.30, N: 10.39.

EXAMPLE 16

(±)-1-(2,2-Dimethylethoxycarbonyl)-2-methyl-4-oxopiperidine

Step 1

The methodology of D. L. Comins and J. D. Brown, Tetrahedron Letters, 1986, pp 4549–4552 was used: To a stirred solution of 2.5 g of 4-methoxypyridine in 75 mL of anhydrous tetrahydrofuran cooled to −23° C. under a nitrogen atmosphere was added 8 mL of 3M methylmagnesium chloride in tetrahydrofuran followed by 4 g of benzylchloroformate, keeping the internal temperature below −20° C. After stirring for 4 h at −25°±5° C., the reaction was quenched with 100 mL of 1N HCl and extracted with 5×100 mL portions of ether. The combined extracts were dried over $MgSO_4$ and concentrated under reduced pressure. Further drying under vacuum gave 5.1 g of 2(R,S)-methyl-1-(benzyloxycarbonyl)-2,3-dihydro-4-pyridone as a greenish oil: TLC (25% EtOAc in hexane); $^1$H NMR (400 MHz, $CDCl_3$) 7.75 (d, 1H), 7.4 (s, 5H), 5.30 (d, 1H), 5.26 (s, 2H), 4.7 (m, 1H), 2.82 (dd, 1H), 2.38 (d, 2H), 1.25 (t, 3H).

Step 2

A mixture of 1.1 g of the crude 2(R,S)-methyl-1-(benzyloxycarbonyl)-2,3-dihydro-4-pyridone, 200 mL of ethyl acetate, 1 g of di-tert-butyldicarbonate and 1 g of 10% palladium on carbon was shaken under 55 psi of hydrogen for 24 h. The mixture was filtered, concentrated under reduced pressure, and purified by low pressure chromatography on silica gel eluting with 40% ethyl acetate in hexane. There was obtained first 0.20 g of (±)-1-(2,2-dimethylethoxycarbonyl)-2-methyl-4-oxopiperidine: $^1$H NMR (400 MHz, $CDCl_3$) 4.65 (m, 1H), 4.2 (m, 1H), 3.3 (m, 1H), 2.65 (dd, 1H), 2.45 (m, 1H), 2.3 (m, 1H), 2.2 (dd, 1H), 1.45 (s, 9H), 1.14 (d, 3H). Later fractions gave 0.50 g of the (±)-1-(2,2-dimethylethoxycarbonyl)-2-methyl-4-hydroxypiperidine: $^1$H NMR (400 MHz, $CDCl_3$) 4.3 (m, 1H), 4.15 (t, 1H), 3.8 (m, 1H), 3.25 (m, 1H), 2.15 (s, 1H), 2.8 (m, 1H), 1.65 (m, 3H), 1.42 (s, 3H), 1.25 (d, 3H).

EXAMPLE 17

1,3-Dihydro-1-{1'-[1"-(2'''.2'''-dimethylethoxycarbonyl)-2"-methylpiperidin-4"-yl]piperidin-4'-yl}-2H-benzimidazol-2-one A mixture 0.20 g of (±)-1-(2,2-dimethylethoxycarbonyl)-2-methyl-4-oxopiperidine, 0.40 g of 4-(2-oxo-1-benzimidazolinyl)piperidine, 5 mL of 1,2-dichloroethane, 0.1 mL of glacial acetic acid and 0.40 g of sodium triacetoxyborohydride was stirred at room temperature for 48 h. The reaction mixture was poured into 200 mL chloroform and 200 mL saturated aqueous $Na_2CO_3$ and the layers separated. The aqueous layer was extracted with 2×25 mL of chloroform and the combined organic layers dried over $MgSO_4$ and concentrated under reduced pressure. Trituration of the crude product with ether-hexane 0.13 g of 1,3-dihydro-1-{1'-[1"-(2'",2'"-dimethylethoxycarbonyl)-2"-methylpiperidin-4"-yl]piperidin-4'-yl}-2H-benzimidazol-2-one: 7.23 (m, 1H), 7.1 (m, 1H), 7.0 (m, 2H), 4.4 (m, 1H), 3.9 (m, 1H), 3.8 (m, 1H), 3.1 (m, 3H), 2.8 (br m, 1H), 2.6 (m, 1H), 2.5 (m, 3H), 2.25 (m, 1H), 1.9 (m, 3H), 1.6 (m, 1H), 1.42 (s, 9H), 1.24 (d, 3H).

EXAMPLE 18

1,3-Dihydro-1-{1'-[1"-(3'"-pyridinecarbonyl)-2"-methyl-piperidin-4"-yl]-piperidin-4'-yl}-2H-benzimidazol-2-one Step 1

A stirred solution of 0.13 g of 1,3-dihydro-1-{1'-[1"-(2'",2'"-dimethylethoxycarbonyl)-2"-methylpiperidin-4"-yl]piperidin-4'-yl}-2H-benzimidazol-2-one in 15 mL of 1N HCl was heated to reflux for 3 h, cooled and concentrated to dryness. The residue was partitioned between 3 mL of 2N NaOH and 5×50 mL of methylene chloride. The combined organic extracts were dried over MgSO$_4$ and concentrated under reduced pressure. After drying under vacuum, there was obtained 0.1 g of 1,3-dihydro-1-{1'-[2"-methylpiperidin-4"-yl]piperidin-4'-yl}-2H-benzimidazol-2-one as a gum (racemic mixture of diastereomers).

Step 2

To a stirred solution of 0.1 g of 1,3-dihydro-1-{1'-[2"-methylpiperidin-4"-yl]piperidin-4'-yl}-2H-benzimidazol-2-one and 0.2 mL of triethylamine in 250 mL of dichloromethane was added 0.50 g of nicotinoyl chloride hydrochoride. After 2 h, 50 mL of dilute aqueous ammonia was added and the mixture stirred for an additional 30 min. The organic layer was separated, the aqueous layer saturated with sodium chloride and extracted with two additional 20 mL portions of chloroform and the combined organic extracts dried over MgSO$_4$ and concentrated under reduced pressure. Purification of the residue by preparative thin chromatography on silica gel eluting with 160:50:10 CHCl$_3$:MeOH:NH$_4$OH followed by trituration with ether gave 90 mg of 1,3-dihydro-1-{1'-[1"-(3'"-pyridinecarbonyl)-2"-methyl-piperidin-4"-yl]-piperidin-4'-yl}-2H-benzimidazol-2-one as a white solid: $^1$H NMR (400 MHz, CDCl$_3$) 10.4 (s, 1H), 8.66 (d, 2H), 7.77 (dt, 1H), 7.38 (dd, 1H), 7.25 (m, 1H), 7.1 (m, 1H), 7.05 (m, 2H), 4.4 (br m, 2H), 3.7 (br m, 1H), 3.4 (br m, 1H), 3.2 (br d, 1H), 3.1 (m, 2H), 2.8 (br m, 1H), 2.65 (br m, 1H), 2.5 (m, 2H), 2.22 (q, 2H), 2.0 (br d, 1H), 1.9 (br d, 2H), 1.75 (br m, 1H), 1.4 (2×d, 3H). The citrate salt precipitated from ethyl acetate/methanol: Analysis calculated for C$_{26}$H$_{34}$N$_6$O$_3$.1.0 C$_6$H$_8$O$_7$.0.8CHCl$_3$.1.0H$_2$O: C: 51.01, H:5.53, N: 9.66; found C: 51.12, H: 5.76, N: 9.28. HPLC analysis on C-18 with a gradient of 60:40 to 0:100, aqueous 0.12% ammonium formate:methanol indicated a ratio of 83:17 cis:trans isomers, consistent with the known preference for equatorial attack of hydride during reductive amination of cyclic ketones.

EXAMPLE 19

1,3-Dihydro-1-(8'-azabicyclo[3.2.1]octan-3'α-yl)-2H-benzimidazol-2-one

Step 1

A mixture of 8 g of 1-carbethoxy-4-tropinone, 8 g of 1,2-phenylenediamine, 250 mL of absolute methanol, 2.5 mL of acetic acid and 2.5 g of sodium cyanoborohydride was stirred at room temperature overnight. The resulting mixture was concentrated to dryness under reduced pressure and partitioned between 3×200 mL of chloroform and 50 mL of sat'd. sodium carbonate in an ice bath while a solution of 50 mL of 1.93M phosgene in toluene was added. The resulting mixture was allowed to warm to room temperature and stirred for 24 h, diluted with 250 mL of ethyl acetate. The layers were separated and the organic layer dried over MgSO$_4$ and concentrated under reduced pressure. Low pressure chromatography over silica gel, eluting with ethyl acetate gave, after trituration with hexane-ethyl acetate, 7.33 g of 1,3-dihydro-1-(1'-ethoxycarbonyl-8'-azabicyclo[3.2.1] octan-3'α-yl) -2H-benzimidazol-2-one as a white solid: $^1$H NMR (400 MHz, CDCl$_3$) 9.84 (s, 1H), 7.05 (m, 4H), 4.5 (br m, 2H), 4.4 (m, 1H), 4.2 (br m, 2H), 2.5 (br s, 2H), 2.1 (br m, 4H), 1.9 (br d, 2H), 1.5 (t, 3H).

Step 2

A stirred mixture of 7.33 g of 1,3-dihydro-1-(1'-ethoxycarbonyl-8'-azabicyclo[3.2.1]octan-3'α-yl)-2H-benzimidazol-2-one, 50 mL of dioxane and 40 mil of 2N NaOH was heated to reflux for 12 h. After cooling in an ice bath, 5 g of ammonium chloride was added and the mixture was extracted with 3×200 mL of 10% THF in ethyl acetate. The combined extracts were dried over MgSO$_4$ and concentrated under reduced pressure trituration with hexane-ether-ethyl acetate gave, in two crops, 5.53 g of 1,3-dihydro-1-(8'-azabicyclo[3.2.1]octan-3'α-yl)- 2H-benzimidazol-2-one as a white solid: $^1$H NMR (400 MHz, CDCl$_3$) 7.05 (m, 4H), 4.6 (m, 1H), 3.75 (d, 2H), 2.95 (br s, 2H), 2.35, (dt, 2H), 2.05 (t, 2H), 1.9 (m, 4H).

EXAMPLE 20

(1'"R) 1,3-Dihydro-1-{1'-[8"-(1'"-(5""-pyrimidinyl)-1'"-ethyl)piperidin-4"-yl]-8'-azabicyclo[3.2.1]octan-3'α-yl}-2H-benzimidazol-2-one A mixture of 0.125 g of 1-(1R-(5-pyrimidinyl)-ethyl)-2R-methyl-4-oxopiperidine, 0.240 g of 1,3-dihydro-1-(8'-azabicyclo[3.2.1]octan-3'α-yl)-2H-benzimidazol-2-one, 5 mL of 1,2-dichloroethane, 5 mL of tetrahydrofuran, 0.1 mL of glacial acetic acid and 0.4 g of sodium triacetoxyborohydride was stirred at room temperature for 24 h. The reaction mixture was partitioned between 100 mL chloroform and 5 mL 20% NaOH and the organic layer dried over MgSO$_4$ and concentrated under reduced pressure. Trituration with ether-ethyl acetate-hexane gave 0.275 of (1'"R) 1,3-dihydro-1-{1'-[8"-(1'"-(5""-pyrimidinyl)-1'"-ethyl) piperidin-4"-yl]-8'-azabicyclo[3.2.1]octan-3'α-yl}-2H-benzimidazol-2-one as a buff solid: $^1$H NMR (400 MHz, CDCl$_3$) 9.15 (s, 1H), 8.7 (s, 2H), 7.05 (m, 3H), 4.75 (m, 1H), 3.6 (br m, 2H), 3.55 (m, 1H), 2.95 (br d, 1H), 2.8 (br d, 1H), 2.35 (dd, 2H), 2.0 (complex m, 6H), 1.8 (m, 2H), 1.7 (dd, 2H), 1.63 (br m, 1H), 1.5 (m, 2H), 1.4 (d, 3H); The citrate salt precipitated from ethyl acetate/methanol: Analysis calculated for C$_{25}$H$_{32}$N$_6$O.1.05C$_6$H$_8$O$_7$.1.0H$_2$O: C: 57.62, H: 6.89, N: 12.88; found C: 58.01, H: 6.89, N: 12.56.

EXAMPLE 21

1,3-Dihydro-1-(8'-azabicyclo[3.2.1]octan-3'β-yl)-2H-benzimidazol-2-one

Step 1

To a stirred solution of 10 g of 1-carbethoxy-4-tropinone in 50 mL of anhydrous tetrahydrofuran cooled to −78° C. under nitrogen atmosphere was added 75 mL of 1M lithium tri-sec-butylborohydride in tetrahydrofaran, keeping the internal temperature below −68° C. When the addition was complete, the mixture was stirred for 15 min at −78° C., quenched with 10 mL of water and warmed to 0° C. in an ice bath. The borane complex was decomposed by dropwise

19 addition of 30 mL of 2N NaOH and 40 mL of 15% hydrogen peroxide. After 15 min, the mixture was extracted with 6×200 mL of ethyl acetate and the combined organic extracts dried over $MgSO_4$ and concentrated under reduced pressure. Repeated azeotropic distillations with methanol to remove borate esters and trituration with hexane-ether gave 9.25 g of 1-carbethoxy-4α-tropinol as crystalline solid: $^1H$ NMR (400 MHz, $CDCl_3$) 4.25 (br m, 2H), 4.15 (q and overlapping br m, 3H), 2.18 (q, 2H), 2.1 (br m, 2H), 1.94 (m, 2H), 1.73 (d, 2H), 1.6 (br s, 1H), 1.25 (t, 3H).

Step 2

To an ice cold, stirred solution of 4.0 g of 1-carbethoxy-4-α-tropinol and 10 mL of triethylamine in 280 mL of methylene chloride was added 2.0 mL of methanesulfonyl chloride dropwise, keeping the internal temperature below 5° C. After stirring for 30 min with the ice bath removed, the mixture was partitioned between 6×100 mL of chloroform and 100 mL of water. The combined extracts were washed with 100 mL of 1N HCl, 100 mL of sat'd. sodium carbonate, dried over $MgSO_4$ and concentrated under reduced pressure. Drying under vacuum gave 5.5 g of 1-carbethoxy-4α-methylsulfonyloxytropane as an amber oil: $^1H$ NMR (400 MHz, $CDCl_3$) 5.0 (t, 1H), 4.3 (br m, 2H), 4.15 (q, 2H), 3.0 (s, 3H), 2.18 (br m, 2H), 2.05 (m, 6H), 1.3 (t, 3H).

Step 3

A stirred mixture of 5.5 g of 1-carbethoxy-4(α-methylsulfonyloxy-tropane, 6.0 g of sodium azide and 50 mL of anhydrous DMF was heated to 60° C. for 2 days. The mixture was cooled and partitioned between 750 mL of water on 3×150 mL of diethyl ether. The combined ether extracts were washed 3×50 mL of water, dried over $MgSO_4$ and concentrated under reduced pressure. Drying under vacuum gave 5.5 g of 1-carbethoxy-4β-azidotropane as an white solid: $^1H$ NMR (400 MHz, $CDCl_3$) 4.4 (br m, 2H), 4.18 (q, 2H), 3.74 (m, 1H), 2.05 (m, 2H), 1.95 (dd, 2H), 1.65 (m, 6H), 1.25 (t, 3H).

Step 4

A mixture of 4.5 g of the 1-carbethoxy-4β-azidotropane, 300 mL of ethanol and 1 g of 10% palladium on carbon was shaken under 1 atm of hydrogen (balloon) for 18 h. The mixture was filtered and concentrated under reduced pressure. Drying under vacuum gave 4.5 g of 1-carbethoxy-4β-aminotropane as a gum: $^1H$ NMR (400 MHz, $CDCl_3$) 4.3 (br m, 2H), 4.18 (q, 2H), 3.15 (m, 1H), 1.95 (m, 2H), 1.82 (m, 2H), 1.7 (m, 2H), 1.4 (m, 2H), 1.30 (t, 3H).

Step 5

A mixture of 3.6 g of 2-fluoronitrobenzene, 4.5 g of 1-carbethoxy-4β-aminotropane, 3 g of sodium carbonate,15 mL of cyclohexanol was heated to 160° C. for 2 h. After cooling, the mixture was partitioned between 4×100 mL of ethyl acetate and 250 mL of water. The organic extract was dried over $MgSO_4$ and concentrated under reduced pressure. Trituration with hexane gave, in two crops., 5.7 g of 1-carbethoxy-4β-(2-nitrophenylamino)tropane as an orange crystalline solid: $^1H$ NMR (400 MHz, $CDCl_3$) 8.2 (d, 1H), 7.9 (d, 1H), 7.42 (m, 1H), 6.88 (d, 1H), 6.63 (m, 1H), 4.4 (br m, 2H), 4.2 (q, 2H), 4.02 (m, 1H), 2.1 (m, 4H), 1.8 (dd, 2H), 1.7 (br m, 2H), 1.3 (t, 3H).

Step 6

A mixture of 5.7 g of 1-carbethoxy-4β-(2-nitrophenylamino)tropane, 200 mL of tetrahydrofuran, 150 mL of ethanol and 1.2 g of 5% platinum on carbon was stirred under an atmosphere of hydrogen for 7 h. The catalyst was filtered off and the filtrate concentrated to to a pink solid. To an ice cold, stirred solution of the resulting crude 1-carbethoxy-4β-(2-aminophenylamino)tropane in 500 mL of ethyl acetate was added 200 mL of saturated sodium bicarbonate followed by 20 mL of 1.9M phosgene in toluene dropwise over 30 min. After stirring overnight at room temperature, the layers were separated, the aqueous layer extracted with 3×100 mL of ethyl acetate and the combined organic layers dried over $MgSO_4$ and concentrated to dryness. Trituration of the residue with ether gave 5.0 g of 1,3-dihydro-1-(1'-ethoxycarbonyl-8'-azabicyclo[3.2.1] octan-3'β-yl)-2H-benzimidazol-2-one as a buff solid: $^1H$ NMR (400 MHz, $CDCl_3$) 9.85 (br m, 1H), 7.15 (m, 1H), 7.05 (m, 3H), 4.95 (m, 1H), 4.5 (br d, 2H), 4.25 (br d, 2H), 2.5 (br m, 2H), 2.1 (m, 2H), 1.93 (dd, 2H), 1.77 (dd, 2H), 1.35 (t, 3H).

Step 7

A stirred mixture of 4.74 g of 1,3-dihydro-1-(1'-ethoxycarbonyl-8'-azabicyclo[3.2.1]octan-3'β-yl) -2H-benzimidazol-2-one, 100 mL of dioxane and 40 mL of 2N NaOH was heated to reflux for 48 h. After distilling off 60 mL of dioxane over 2 h, the mixture was cooled in an ice bath and 5 g of ammonium chloride was added. The mixture extracted with 3×100 mL of chloroform. The combined chloroform extracts were extracted into 3×50 mL portions of 1N HCl. Drying the chloroform layer over $MgSO_4$ and concentration under reduced pressure gave back 2.3 g of 1,3-dihydro-1-(1'-ethoxycarbonyl -8'-azabicyclo [3.2.1] octan-3'β-yl)-2H-benzimidazol-2-one (starting material). The combined acidic aqueous extracts were basified with 20% NaOH to pH 10 and extracted with 3×100 mL of chloroform. The combined chloroform extracts were dried over $MgSO_4$ and concentrated under reduced pressure. Trituration with ethyl ether gave, in two crops, 1.90 g of 1,3-dihydro-1-(8'-azabicyclo[3.2.1]octan-3'β-yl)-2H-benzimidazol-2-one as a white solid: $^1H$ NMR (400 MHz, $CDCl_3$) 9.4 (br s, 1H), 7.3 (m, 1H), 7.1 (m, 1H), 7.05 (m, 2H), 4.75 (m, 1H), 3.74 (br m, 2H), 2.4 (m, 2H), 1.9 (m, 4H), 1.7 (m, 2H).

EXAMPLE 22

(1'''R) 1,3-Dihydro-1-{1'-[8"-(1'''-(5""-pyrimidinyl)-1'''-ethyl)piperidin-4"-yl]-8'-azabicyclo[3.2.1]octan-3'β-yl}-2H-benzimidazol-2-one A mixture of 0.25 g of 1-(1R-(5-pyrimidinyl)-ethyl)-2R-methyl-4-oxopiperidine, 0.25 g of 1,3-dihydro-1-(8'-azabicyclo[3.2.1]octan-3'62 -yl)-2H-benzimidazol-2-one, 10 mL of 1,2-dichloroethane, 10 mL of tetrahydrofuran, 0.2 mL of glacial acetic acid and 0.4 g of sodium triacetoxyborohydride was stirred at room temperature for 48 h. The reaction mixture was partitioned between 3×100 mL chloroform and 50 mL sat'd. sodium carbonate and the organic layer dried over $MgSO_4$ and concentrated under reduced pressure. Trituration with ether-ethyl gave 0.325 of (1'''R) 1,3-dihydro-1-{1'-[8"-(1'''-(5""-pyrimidinyl)-1'''-ethyl) piperidin-4"-yl]-8'-azabicyclo[3.2.1]octan-3'β-yl}-2H-benzimidazol- 2-one as a white solid: $^1H$ NMR (400 MHz, $CDCl_3$) 9.14 (br s, 1H), 9.12 (s, 1H), 8.37 (s, 2H), 7.77 (m, 1H), 7.05 (m, 3H), 4.7 (m, 1H), 3.62 (br m, 2H), 3.6 (dd, 1H), 3.0 (br d, 1H), 2.84 (br d, 1H), 2.7 (m, 1H), 2.5 (t, 2H), 2.16 (dd, 2H), 2.0 (m, 4H), 1.8 (dd, 2H), 1.75 (br m, 1H), 1.55 (m, 3H), 1.42 (d, 3H); The citrate salt precipitated from ethyl acetate/methanol: Analysis calculated for $C_{25}H_{32}N_6O \cdot 1.0C_6H_8O_7 \cdot 1.0H_2O$: C: 57.93, H: 6.59, N: 13.08; found C: 58.23, H: 6.45, N: 13.45.

EXAMPLE 23

1,3-Dihydro-1-{1'-[1''-(1'''-methylimidazol-5'''-carbonyl)-piperidin-4''-yl]-piperidin-4'-yl}-2H-benzimidazol-2-one Step 1

A mixture of 1.5 g of ethyl 1-methyl-5-imidazolecarboxylate, 5 mL of ethanol and 5 mL of 10% NaOH was stirred at room temperature for 12 h. The mixture was acidified to pH 2 with conc. HCl, diluted with 10 mL of ice water. The precipitated product was collected by filtration in 2 crops. Drying under vacuum gave 843 mg of 1-methyl-5-imidazolecarboxylic acid as a white solid.

Step 2

To a stirred solution of 0.20 g of 1-methyl-5-imidazolecarboxylic acid in 4 nL of DMF, 4 mL of tetrahydrofuran and 0.5 mL of triethylamine cooled to 0° C. was added 0.30 mL of diphenylphosphoryl chloride. A white precipitate formed immediately. After stirring in the cold for 30 min, 0.20 g of 1,3-dihydro-1-{1'-[piperidin-4''-yl] piperidin-4'-yl}-2H-benzimidazol-2-one was added and the mixture allowed to warm and stir for 24 h. The mixture was partitioned between 5 mL of sat'd. sodium carbonate and 2×125 mL of chloroform. The combined organic extracts were dried over $MgSO_4$ and concentrated under reduced pressure. Purification of the residue by preparative thin chromatography on silica gel eluting with 200:50:10 $CHCl_3$:MeOH:$NH_4$OH followed by trituration with ether gave 0.20 g of 1,3-dihydro-1-{1'-[1''-(1'''-methylimidazol-5'''-carbonyl)-piperidin-4''-yl]-piperidin-4'-yl}-2H-benzimidazol-2-one as a white solid: $^1$H NMR (400 MHz, $CDCl_3$) 10.85 (s, 1H), 7.52 (s, 1H), 7.25 (m, 1H), 7.22 (s, 1H), 7.15 (m, 1H), 7.05 (m, 2H), 4.55 (br m, 2H), 4.35 (m, 1H), 3.8 (s, 3H), 3.1 (d, 2H), 3.0 (br m, 2H), 2.65 (br m, 1H), 2.40 (br m, 4H), 1.95 (br d, 2H), 1.85 (br d, 2H), 1.55 (m, 2H). The citrate salt precipitated from ethyl acetate/methanol: Analysis calculated for $C_{22}H_{28}N_6O_2 \cdot 1.3 C_6H_8O_7 \cdot 1.0 CH_3CO_2CH_2CH_3$: C: 54.39, H: 6.27, N: 11.26; found C: 54.03, H: 6.48, N: 11.40.

EXAMPLE 24

(3'S,4'R,1'''S and 3'R,4'S,1'''S) 1,3-Dihydro-1-{1'-[1''-(1'''-phenylethyl)-piperidin-4''-yl]-3'-ethoxycarbonylpiperidin-4'-yl}-2H-benzimidazol-2-one Step 1

To a stirred mixture of 1.2 g of (S)-(−)-1-phenethylamine, 17 mL of ethanol and 1.36 g of $K_2CO_3$ heated to reflux was added dropwise over 30 min, a solution of 4.0 g of 1,1-dimethyl-4-oxopiperidinium iodide in 20 mL of water. When the addition was complete, the mixture was heated under reflux for an additional 1.5 h, cooled, basified to pH 9 with $K_2CO_3$ and extracted with 3 times with 100 mL portions of methylene chloride. The combined organic extracts were dried over $MgSO_4$ and concentrated under reduced pressure. Chromatography over silica gel, eluting with 1:1 chloroform:ethyl acetate gave 1.2 g of 1-(1S-(phenethyl)-4-oxopiperidine as an oil.

Step 2

A mixture of 0.350 g of 1-(1S-(phenethyl)-4-oxopiperidine, 0.170 g of (±)-trans-1-(3-ethoxycarbonyl-4-piperidinyl)benzimidazol-2H-one, 8 mL of 1,2-dichloroethane, 0.2 mL of glacial acetic acid and 0.8 g of sodium triacetoxyborohydride was stirred at room temperature for 48 h. The reaction mixture was partitioned between 3×50 mL chloroform and 20 mL saturated aqueous $Na_2CO_3$. The combined organic layers were dried over $MgSO_4$ and concentrated under reduced pressure. Purification of the residue by preparative thin chromatography on silica gel eluting with 90:10 methylene chloride:methanol followed by trituration with ether gave 0.20 g of (3'S,4'R,1'''S and 3'R,4'S,1'''S) 1,3dihydro-1-{1'-[1''-(1'''-phenylethyl)-piperidin-4''-yl]-3'-ethoxycarbonylpiperidin-4'-yl}-2H-benzimidazol-2-one as a mixture of diastereomers: $^1$H NMR (400 MHz, $CDCl_3$) 10.45 (s, 1H), 7.3 (m, 4H), 7.25 (m, 1H), 7.2 (m, 1H), 7.1 (m, 1H), 7.05 (m, 2H), 4.4 (br m, 1H), 3.9 (q, 2H), 3.6 (br m, 1H), 3.42 (m, 1H), 3.25 (d, 1H), 3.15 (d, 1H), 3.05 (d, 1H), 2.9 (d, 1H), 2.45 (complex m, 4H), 2.0 (t, 1H), 1.85 (m, 2H), 1.7 (m, 2H), 1.6 (m, 1H), 1.38 (d, 3H), 0.95 (t, 3H); The citrate salt precipitated from ethyl acetate/methanol: Analysis calculated for $C_{24}H_{32}N_6O \cdot 1.35 C_6H_8O_7 \cdot 1.0 CH_3CO_2CH_2CH_3$: C: 58.44, H: 6.70, N: 6.80; found C: 58.37, H: 6.84, N: 6.92.

EXAMPLE 25

Radioligand and Binding Studies

The affinity of muscarinic antagonists for m1–m5 receptors expressed in chinese hamster ovary cells (CHO) were determined using the technique described by Doije et al., J. Pharmacol. Exp. Ther. 256: 727–733 (1991).

When 80–100% confluent, CHO cells were harvested, and transferred to centrifuge tubes containing CHO buffer (20 mM HEPES at pH 7.4 containing 5 mM $MgCl_2$). The cells were homogenized, using a Brinkman Polytron homogenizer for 30 seconds at a setting of 5, on ice. The homogenate was centrifuged at 40,000× g for 15 minutes at 4° C. in a Beckman J2-21M centrifuge.

The supernatant was discarded and the homogenization/centrifugation step repeated once. Pelleted membranes were resuspended in CHO buffer to a concentration of one flask harvested (75 cm$^2$) per mL of buffer, mixed well and aliquoted in cryovials (1 mL/vial). The vials were stored at −70° C. until used in the assay. The binding incubation was done in polypropylene macrowell tube strips in a final volume of 0.5 mL of HEPES buffer (20 mM; pH 7.4 containing 5 mM $MgCl_2$) containing 0.1 mL of cell membrane suspension, 3H-N-methylscopolamine (NEN Corporation, NET-636, 70–87 C/mmole) at a final concentration of approximately 0.2 nM and the competing drug in a varying range of concentrations or vehicle. After the addition of the cell homogenate the tubes were agitated on a vortex mixer and then placed in a water bath at 32° C. After 90 minutes of incubation, the membranes were harvested on a Skatron filtermat (#11734) or a Wallac filtermat (#205-404) using three washes of HEPES buffer (4° C.). The radioactivity on the filters was counted in a Packard 2200CA scintillation counter or in a Wallac 1205 Betaplate scintillation counter. Specific binding was defined as the difference in binding observed in the presence and absence of 10 micromolar atropine and accounted for at least 80% of total binding. $K_i$ values were calculated using the program LIGAND. Compounds displayed $K_i$ values at m1, m2 and m4 in the range of 1 nM to 5,000 nM. All compounds described herein displayed typically greater than 300-fold less potency at the m3 receptor subtype, in the range of 300 nM to 114,000 nM.

EXAMPLE 26 m1 receptor antagonist activity on the rabbit vas deferens

The technique described by Feifel et al., Brit. J. Pharmacol. 99: 455–460 (1990) was used as follows: Male Hazelton New Zealand White rabbits weighing 1.5–3 kg, are euthanized (phenobarbital sodium, 85 mg/kg, i. v.). An abdominal incision is made and the vas deferens are removed. The tissues are placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 25 mM; dextrose, 11 mM] warmed to 30° C. Each tissue is cut into three 2-cm segments: proximal to the prostate, a middle section, and distal to the prostate. Only the first two segments are used. Tissue segments are attached to platinum electrodes with 4-0 surgical silk and placed in a 10 mL jacketed tissue bath containing Krebs buffer at 30° C., bubbled with 5% $CO_2$/95% $O_2$. The tissues are connected to a Statham-Gould force transducer; 0.75 gram of tension is applied and the tissues are electrically stimulated. [EFS parameters are 0.05 Hz; 0.5 ms duration; voltage is set to 30% of 50 V at 25 ohms and increased until a supramaximal voltage is achieved.] The contractions are recorded on a Gould strip chart recorder. The tissues are washed every 20 minutes and allowed to equilibrate. A concentration response curve to the selective m1 receptor agonist McN-A-343 is determined. Tissues are washed every 20 minutes for 60 minutes. The vehicle or compound is added to the bath and the tissues are incubated for 30 minutes, then the McN-A-343 concentration response is repeated. $EC_{50}$ values are determined for both vehicle and tissues treated with the compound before and after treatment. Antagonist dissociation constants ($K_b$) are calculated by the dose-ratio method. Compounds displayed $K_b$ values at m1 in the range of 5 to 100 nM.

EXAMPLE 27 m2 receptor antagonist activity on the guinea pig left atria

The technique described by Feifel et al., Brit. J. Pharmacol. 99: 455–460 (1990) was used as follows: Duncan-Hartley guinea pigs (Hazelton) weighing 300–600 g, are asphyxiated with $CO_2$. The abdomen is opened and the left atria is rapidly removed. The tissues are placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 25 mM; dextrose, 11 mM] warmed to 37° C. Each atria is attached to platinum electrodes with 4-0 surgical silk and placed in a 10 mL jacketed tissue bath containing Krebs buffer at 37° C., bubbled with 5% $CO_2$/95% $O_2$. The tissues are connected to a Statham-Gould force transducer; 0.75 gram of tension is applied and the tissues are electrically stimulated. [EFS parameters are 3 Hz; 4 ms duration; voltage is set to 5 V.] The contractions are recorded on a Gould strip chart recorder. The tissues are washed every 20 minutes and allowed to equilibrate. A concentration response curve to the agonist carbachol is determined. Tissues are washed every 20 minutes for 60 minutes. The vehicle or compound is added to the bath and the tissues are incubated for 30 minutes, then the carbachol concentration response is repeated. $EC_{50}$ values are determined for both vehicle and compound treated tissues before and after treatment. Antagonist dissociation constants ($K_b$) are calculated by the dose-ratio method. Compounds displayed $K_b$ values at M2 in the range of 5 to 100 nM.

EXAMPLE 28

M3 receptor antagonist activity on the guinea pig ileum longitudinal muscle

The technique described by Feifel et al., Brit. J. Pharmacol. 99: 455–460 (1990) was used as follows: Duncan-Hartley guinea pigs (Hazelton) weighing 300–600 g, are asphyxiated with $CO_2$. The abdomen is opened and the caecum and the distal end of the ileum are identified. The ileum is removed and 5 cm of the terminal end (proximal to the caecum) is discarded. The lumen of the remainder is flushed with oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 25 mM; dextrose, 11 mM] warmed to 30° C. The ileum is cut into 2.5 cm segments and each segment is mounted on a glass pipette. A scalpel is used to lightly cut the surface of the tissue and a cotton swab used to tease the longitudinal muscle free from the underlying circular muscle. Longitudinal muscle segments are attached to glass tissue holders with 4-0 surgical silk and placed in a 10 mL jacketed tissue bath containing Krebs buffer at 30° C., bubbled with 5% $CO_2$/95% $O_2$. The tissues are connected to a Statham-Gould force transducer. One gram of tension is applied and the contractions are recorded on a Gould strip chart recorder. The tissues are washed every 20 minutes and allowed to equilibrate. A concentration response curve to the agonist carbachol is determined. Tissues are washed every 20 minutes for 60 minutes. The vehicle or compound is added to the bath and the tissues are incubated for 30 minutes, then the carbachol concentration response is repeated. $EC_{50}$ values are determined for both vehicle and tissues treated with the compound before and after treatment. Antagonist dissociation constants ($K_b$) are calculated by the dose-ratio method. Compounds displayed $K_b$ values at M3 in the range of 3900 to 24000 nM.

EXAMPLE 29 m1 and m3 receptor antagonist activity on the human muscarinic receptors expressed in CHO cells Preconfluent CHO cells were labeled for 24 hours with 4 µC/mL of [$^3$H] myo-inositol (specific activity 15–20 C/mmole). The cells were detached from flasks using 1 mM EDTA in phosphate buffer saline, centrifuged for 5 minutes at 200× g, and resuspended in assay buffer (116 mM NaCl; 10 mM LiCl; 4.7 mM KCl; 1.2 mM $MgSO_4$; 2.5 mM $CaCl_2$; 1.2 mM $KH_2PO_4$; 5 mM $NaHCO_3$; 11 mM dextrose, 20 mM HEPES; pH 7.4 at 37° C.) to the desired volume. Four hundred microliters of the cell suspension (approximately $2\times10^6$ cells) was added to tubes containing buffer or compound and left at room temperature for 30 minutes. Muscarinic agonist (carbachol) was then added and the cells incubated for 30 minutes at 37° C. The reaction was stopped using an acid solution (12% perchloric acid/3 mM EDTA/1 mM diethylenetriamine pentaacetic acid) and the tubes placed on ice for 15 minutes. The samples were then neutralized with 3M KOH/0.25M 2-(N-morpholino)ethane sulfonic acid/0.25M 3-(N-morpholino) propane sulfonic acid and centrifuged at 3000× g for 15 minutes. Five hundred microliters of each supernatant was diluted to 5.5 mL with water and the entire tube contents applied to anion exchange columns. The columns are sequentially washed with 5 mL of $H_2O$, 15 mL of 60 mM ammonium formate/5 mM borax and 8 mL of 200 mM ammonium formate/5 mM borax. The radioactivity in the last eluate was determined by liquid scintillation counting and taken as the amount of [$^3$H]-inositol monophosphate formed during the incubation. Two different types of experiments were performed: $IC_{50}$ values for compounds where calculated using a fixed concentration of carbachol, or $K_b$ values were generated by performing carbachol concentration-response curves in the absence and presence of a fixed concentration of compound.

Compounds displayed $K_b$ values at m1 and m3 in the range of 1 to 100 nM at m1 and 4,000 to 20,000 at m3.

EXAMPLE 30 m2 receptor antagonist activity on the human muscarinic receptors expressed in CHO cells Preconfluent CHO cells were harvested using 1 mM EDTA in phosphate buffer saline and washed one time by centrifugation in a HEPES buffered physiological salt solution. The cell concentration was adjusted to 3.3×10⁶ cells / mL in the HEPES buffer containing 1.3 micromolar isobutylmethylxanthine. Three hundred microliters of the cell suspension was added to tubes containing compound and incubated for 15 minutes at room temperature. Muscarinic agonist (50 microliters of carbachol; 1 micromolar final concentration) was then added followed by 20 microliters of 200 µM forskolin and the tubes were incubated at 30° C. for an additional 15 minutes. The reaction was stopped by placing the tubes in boiling water for 5 minutes. The tubes were cooled on ice and then centrifuged at 12,000×g for 10 minutes. Fifty microliters of each supernatant was then analyzed for cAMP using a commercially available radio-immunoassay kit following the manufacturer's instructions. Two different types of experiments were performed: $IC_{50}$ values for compounds where calculated using a fixed concentration of carbachol, or $K_b$ values were generated by performing carbachol concentration-response curves in the absence and presence of a fixed concentration of compound. Compounds displayed $K_b$ values at m2 in the range of 1 to 100 nM.

What is claimed is:

1. A compound of structural formula I

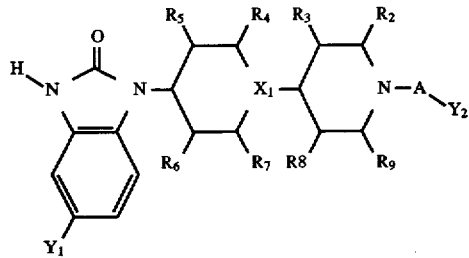

or pharmaceutically acceptable salts thereof, or diastereomers, enantiomers or mixtures thereof;
wherein:
$R_2-R_9$ are independently H, alkyl, halo, alkoxy, OH, HOCH2-, aryl, 3-pyridyl, 5-pyrimidinyl, alkoxycarbonyl, amino, dialkylamino, alkene, thioalkyl, or alkylamino; alternatively, $R_4$ and $R_7$ or $R_2$ and $R_9$ may be connected as an ethylene bridge to form a bicyclic heterocycle;

$Y_1$ is H, alkyl, halo, alkylamino, dialkylamino, alkoxy, alkoxyamino, or amino;

$Y_2$ is heterocycle;

A is $CHR_1$, $C(R_1)_2$ or carbonyl;

$R_1$ is alkyl, alkoxy, aryl, heteroaryl, or heterocycle; and $X_1$ is N or CH, with the proviso that when $X_1$ is N or CH, A cannot be carbonyl and when $X_1$ is CH, $R_1$ cannot be alkyl.

2. The compound of claim 1 wherein:
$R_2-R_9$ are independently H, alkyl, or halo;
$Y_1$ is H, alkyl, or halo;
$Y_2$ is 5-pyrimidinyl, 3-pyridyl, or 1-methyl-5-imidazolyl;
$R_1$ is alkyl, alkoxy, phenyl, 5-pyrimidinyl, 3-pyridyl, or 1-methyl-5-imidazolyl; and $X_1$ is N.

3. The compound:
(3"S,4"R,1"'R and 3"R,4"S,1"'R) 1,3-Dihydro-1-{1'-[1"-(1"'-(5""-pyrimidinyl)-1"'-ethyl)-3"-methylpiperidin-4"-yl]-piperidin-4'-yl}-2H-benzimidazol-2-one;
(3'R,4'R,1"'R and 3'S,4'S,1"'R) 1,3-Dihydro-1-{1'-[1"-(1"'-(5""-pyrimidinyl)-1"'-ethyl)-piperidin-4"-yl]-3'-methylpiperidin-4'-yl}-2H-benzimidazol-2-one;
(3'S,4'R,1"'R and 3'R,4'S,1"'R) 1,3-Dihydro-1-{1'-[1"-(1"'-(5""-pyrimidinyl)-1"'-ethyl)-piperidin-4"-yl]-3'-methylpiperidin-4'-yl}-2H-benzimidazol-2-one;
(3'R,4'R,1"'R and 3'S,4'S,1"'R) 1,3-Dihydro-1-{1'-[1"-(1"'-(5""-pyrimidinyl)-1"'-ethyl)-piperidin-4"-yl]-3'-ethoxycarbonylpiperidin-4'-yl}-2H-benzimidazol-2-one;
(3'S,4'R,1"'R and 3'R,4'S,1"'R) 1,3-Dihydro-1-{1'-[1"-(1"'-(5""-pyrimidinyl)-1"'-ethyl)-piperidin-4"-yl]-3'-ethoxycarbonylpiperidin-4'-yl}-2H-benzimidazol-2-one;
(2"R,4"S,1"'R and 2"R,4"R,1"'R) 1,3-Dihydro-1-{1'-[1"-(1"'-(5""-pyrimidinyl)-1"'-ethyl)-2"-methyl-piperidin-4"-yl]-piperidin-4'-yl}-2H-benzimidazol-2-one;
(2"S,4"S,1"'R) 1,3-Dihydro-1-{1'-[1"-(5""-pyrimidinyl)-1"'-ethyl)-2"-methyl-piperidin-4"-yl]-piperidin-4'-yl}-2H-benzimidazol-2-one;
(2"S,4"R,1"'R) 1,3-Dihydro-1-{1'-[1"-(1"'-(5""-pyrimidinyl)-1"'-ethyl)-2"-methyl-piperidin-4"-yl]-piperidin-4'-yl}-2H-benzimidazol-2-one;
(3'S,4'R,1"'S and 3'R,4'S,1"'S) 1,3-Dihydro-1-{1'-[1"-(1"'-phenylethyl)-piperidin-4"-yl]-3'-ethoxycarbonylpiperidin-4'-yl}-2H-benzimidazol-2-one;
(3"S,4"R,1"'R) 1,3-Dihydro-1-{1'-[1"-(1"'-(5""-pyrimidinyl)-1"'-ethyl)-3"-methylpiperidin-4"-yl]-piperidin-4'-yl}-2H-benzimidazol-2-one;
(3"R,4"S,1"'R) 1,3-Dihydro-1-{1'-[1"-(1"'-(5""-pyrimidinyl)-1"'-ethyl)-3"-methylpiperidin-4"-yl]-piperidin-4'-yl}-2H-benzimidazol-2-one;
(1"'R) 1,3-dihydro-1-{1'-[8"-(1"'-(5""-pyrimidinyl)-1"'-ethyl)piperidin-4"-yl]-8-azabicyclo[3.2.1]octan-3α-yl}-2H-benzimidazol-2-one;
(1"'R) 1,3-dihydro-1-{1'-[8"-(1"'-(5""-pyrimidinyl)-1"'-ethyl)piperidin-4"-yl]-8-azabicyclo[3.2.1]octan-3β-yl}-2H-benzimidazol-2-one.

4. A method for the treatment of abnormal increase in eye axial length in an animal in need thereof, which comprises the step of ocularly administering to said animal a pharmacologically effective amount of a muscarinic pharmacological agent of claim 1.

5. A method for the treatment of abnormal increase in eye axial length in an animal in need thereof, which comprises the step of ocularly administering to said animal a pharmacologically effective amount of a muscarinic pharmacological agent according to claim 1 known to be selective for m1, m2 and m4 receptors, but less active at m3 receptors.

6. A method for the prevention of abnormal increase in eye axial length in an animal in need thereof, which comprises the step of ocularly administering to said animal a pharmacologically effective amount of a muscarinic pharmacological agent according to claim 1.

7. A method for the prevention of abnormal increase in eye axial length in an animal in need thereof, which comprises the step of ocularly administering to said animal a pharmacologically effective amount of a muscarinic pharmacological agent according to claim 1 known to be selective for m1, m2 and m4 receptors, but less active at m3 receptors.

8. A method of alleviating the development of amblyopia in the eye of an animal in need thereof, which comprises administering to such an animal a pharmacologically effective amount of a compound of claim 1.

9. A method of controlling the development of amblyopia in the eye of an animal in need thereof, which comprises administering to such an animal a pharmacologically effective amount of a compound of claim 1.

10. A composition useful for the treatment of abnormal increase in eye axial length in an animal in need thereof, which comprises a pharmacologically effective amount of a muscarinic pharmacological agent of claim 1 in a carrier or diluent buffered to a pH suitable for ocular administration.

11. A composition useful for the prevention of abnormal increase in eye axial length in an animal in need thereof, which comprises a pharmacologically effective amount of a muscarinic pharmacological agent of claim 1, in a carrier or diluent buffered to a pH suitable for ocular administration.

12. A composition useful for the treatment of abnormal increase in eye axial length in an animal in need thereof, which comprises a pharmacologically effective amount of a muscarinic pharmacological agent of claim 1, known to be selective for m1, m2 and m4 receptors, but less active at m3 receptors, in a carrier or diluent buffered to a pH suitable for ocular administration.

* * * * *